US012053442B2

(12) United States Patent
Becker et al.

(10) Patent No.: US 12,053,442 B2
(45) Date of Patent: Aug. 6, 2024

(54) METHODS AND COMPOSITIONS FOR NEUROPROTECTION

(71) Applicant: The Feinstein Institutes for Medical Research, Manhasset, NY (US)

(72) Inventors: Lance Becker, Port Washington, NY (US); Rishabh Charan Choudhary, Queens Village, NY (US)

(73) Assignee: THE FEINSTEIN INSTITUTES FOR MEDICAL RESEARCH, Manhasset, NY (US)

( * ) Notice: Subject to any disclaimer, the term of this patent is extended or adjusted under 35 U.S.C. 154(b) by 52 days.

(21) Appl. No.: 17/527,987

(22) Filed: Nov. 16, 2021

(65) Prior Publication Data
US 2022/0151958 A1  May 19, 2022

Related U.S. Application Data

(60) Provisional application No. 63/114,786, filed on Nov. 17, 2020.

(51) Int. Cl.
| | | |
|---|---|---|
| A61K 31/155 | (2006.01) |
| A61K 31/122 | (2006.01) |
| A61K 31/165 | (2006.01) |
| A61K 31/198 | (2006.01) |
| A61K 31/375 | (2006.01) |
| A61K 31/4152 | (2006.01) |
| A61K 31/4709 | (2006.01) |
| A61K 31/506 | (2006.01) |
| A61K 31/765 | (2006.01) |
| A61K 38/13 | (2006.01) |
| A61K 47/22 | (2006.01) |
| A61P 9/10 | (2006.01) |

(52) U.S. Cl.
CPC .......... *A61K 31/155* (2013.01); *A61K 31/122* (2013.01); *A61K 31/165* (2013.01); *A61K 31/198* (2013.01); *A61K 31/375* (2013.01); *A61K 31/4152* (2013.01); *A61K 31/4709* (2013.01); *A61K 31/506* (2013.01); *A61K 31/765* (2013.01); *A61K 38/13* (2013.01); *A61K 47/22* (2013.01); *A61P 9/10* (2018.01)

(58) Field of Classification Search
None
See application file for complete search history.

(56) References Cited

U.S. PATENT DOCUMENTS

| | | | | |
|---|---|---|---|---|
| 2006/0121016 A1* | 6/2006 | Lee | ........................ | A61K 47/10 424/94.4 |
| 2012/0282227 A1* | 11/2012 | Katz | ........................ | A61P 9/00 514/10.9 |

FOREIGN PATENT DOCUMENTS

CA       2984407 A1    5/2018

OTHER PUBLICATIONS

Choudhary et al. "Multi-Drug Cocktail Therapy Improves Survival and Neurological Function after Asphyxial Cardiac Arrest in Rodents" Cells 12:1548. (Year: 2023).*
Choudhary et al. "Pharmacological Approach for Neuroprotection After Cardiac Arrest—A Narrative Review of Current Therapies and Future Neuroprotective Cocktail" Frontiers in Medicine 8:636651. (Year: 2021).*
"Rationalizing Combination Therapies," Nat. Med., Editorial, 2017, 23:1113.
Adrie et al., "Successful Cardiopulmonary Resuscitation After Cardiac Arrest as a 'Sepsis-Like' Syndrome," Circulation, 2002, 106, 562-568.
Annborn et al., "Procalcitonin after cardiac arrest—An indicator of severity of illness, ischemia-reperfusion injury and outcome," Resuscitation, 2013, 84:782-787.
Arts et al., "HIV-1 Antiretroviral Drug Therapy," Perspect Med., 2012, 2:a007161, 1-24.
Ascierto et al., "Combination therapy: the next opportunity and challenge of Medicine," J. Transl. Med., 2011, 9:115, 1-3.
Belousova et al., "Intravenous Treatment with Coenzyme Q10 Improves Neurological Outcome and Reduces Infarct Volume After Transient Focal Brain Ischemia in Rats," J. Cardiovasc. Pharmacol., Feb. 2016, 67(2):103-109.
Benjamin et al., "Heart Disease and Stroke Statistics—2019 Update, A Report From the American Heart Association," Circulation, 2019, 139:e56-e528.
Choi et al., "Dose-Independent Pharmacokinetics of Metformin in Rats: Hepatic and Gastrointestinal First-Pass Effects," J. Pharm. Sci., 2006, 95:2543-2552.
Choi et al., "Tissue-Specific Metabolic Profiles After Prolonged Cardiac Arrest Reveal Brain Metabolome Dysfunction Predominantly After Resuscitation," J. Am. Heart Assoc., 2019;8:e012809, 31 pages.
Choudhary et al., "Pharmacological Approach for Neuroprotection After Cardiac Arrest—A Narrative Review of Current Therapies and Future Neuroprotective Cocktail," Frontiers in Medicine, May 18, 2021, 8:636651, 14 pages.
Dell'anna et al., "C-reactive protein levels after cardiac arrest in patients treated with therapeutic hypothermia," Resuscitation, 2014, 85:932-938.

(Continued)

*Primary Examiner* — Sudhakar Katakam
*Assistant Examiner* — Zachary J Miknis
(74) *Attorney, Agent, or Firm* — Carter, DeLuca & Farrell LLP; George Likourezos; Carmella L. Stephens

(57) ABSTRACT

The present disclosure relates to compositions, methods of preparation of the compositions, and methods including administration of said compositions for the prevention of neurological damage associated with cerebral ischemia.

8 Claims, 13 Drawing Sheets

(56) References Cited

OTHER PUBLICATIONS

Donnino et al., "Effective lactate clearance is associated with improved outcome in post-cardiac arrest patients," Resuscitation, 2007, 75, 229-234.

Elmer et al., "The association between hyperoxia and patient outcomes after cardiac arrest: analysis of a high-resolution database," Intensive Care Med., 2015, 41, 49-57.

Ferslew, Kenneth E., Specimen Preparation/Extraction, in: B. S. Levine, Kerrigan, Sarah, ed. Principles of Forensic Toxicology. Fifth ed.: Springer Nature 2020, 109-125.

Han et al., "A rodent model of emergency cardiopulmonary bypass resuscitation with different temperatures after asphyxial cardiac arrest," Resuscitation, 2010, 81(1):93-99.

Han et al., "Early mitochondrial dysfunction in electron transfer activity and reactive oxygen species generation after cardiac arrest," Crit. Care Med., 2008, 36(11:Supp):S447-S453.

Hayashida et al., "Inhaled Gases as Therapies for Post-Cardiac Arrest Syndrome: A Narrative Review of Recent Developments," Front. Med., Jan. 2021, 7:586229, 1-13.

He et al., "N-acetylcysteine alleviates post-resuscitation myocardial dysfunction and improves survival outcomes via partly inhibiting NLRP3 inflammasome induced-pyroptosis," J. Inflamm., 2020;17:25, 1-9.

Ikeda et al., "Thiamine as a neuroprotective agent after cardiac arrest," Resuscitation, 2016; 105:138-144.

Janz et al., "Hyperoxia is associated with increased mortality in patients treated with mild therapeutic hypothermia after sudden cardiac arrest," Crit. Care Med., 2012, 40(12):3135-3139.

Jia et al., "Improvine neurological outcomes post-cardiac arrest in a rat model," Resuscitation, 2008, 76:431-442.

Jiang et al., "Impaired Cerebral Mitochondrial Oxidative Phosphorylation Function in a Rat Model of Ventricular Fibrillation and Cardiopulmonary Resuscitation," Biomed. Res. Int., 2014, 192769, 1-9.

Katz et al., "Effect of a pharmacologically induced decrease in core temperature in rats resuscitated from cardiac arrest," Resuscitation, 2015, 92:26-31.

Kilgannon et al., "Association Between Arterial Hyperoxia Following Resuscitation From Cardiac Arrest and In-Hospital Mortality," JAMA, Jun. 2, 2010, 303(21):2165-2171.

Knapp et al., "Evaluation of Cyclosporine as a Cardio- and Neuroprotective Agent After Cardiopulmonary Resuscitation in a Rat Model," Shock, Jun. 1, 2015, 43(6):576-581.

Kraljevic et al., "Accelerating drug discovery," EMBO Reports, 2004, 5(9):837-842.

Kronick et al., "Part 4: Systems of Care and Continuous Quality Improvement," Circulation, 2015, 132(Suppl 2): S397-S413.

Lamoureux et al., "Abstract 148: Zoniporide Combined with alpha-Methylnorepinephrine Appears Highly Effective for Resuscitation from Cardiac Arrest in a Rat Model of Ventricular Fibrillation," Circulation, Nov. 25, 2014, 130(Supp.2), abstract.

Lee et al., "Better lactate clearance associated with good neurologic outcome in survivors who treated with therapeutic hypothermia after out-of-hospital carciac arrest," Crit. Care, 2013, 17, R260, 1-8.

Li et al., "Combination Treatment with Methylene Blue and Hypothermia in Global Cerebral Ischemia," Mol. Neurobiol., 2018, 55:2042-2055.

Liu et al., "Protective effects of cyclosporine A and hypothermia on neuronal mitochondria in a rat asphyxial cardiac arrest model," American Journal of Emergency Medicine, Mar. 2, 2016, 34(6):1080-1085.

Lundin et al., "Drug therapy in cardiac arrest: a review of the literature," European Hearth Journal—Cardiovascular Pharmacotherapy, 2016 (Nov. 26, 2015), 2(1):54-75.

Mader et al., "Blinded Evaluation of Combination Drug Therapy for Prolonged Ventricular Fibrillation Using a Swine Model of Sudden Cardiac Arrest," Prehosp. Emerg. Care, 2016, 20:390-398.

Marcos et al., "PEG 400-Based Phase Change Materials Nano-Enhanced with Functionalized Graphene Nanoplatelets," Nanomaterials, 2017, 8(16):1-18.

Matsumoto et al., "Prevention of Cerebral Edema and Infarct in Cerebral Reperfusion Injury by an Antibody to Interleukin-9," Lab. Invest., 1997, 77(2):119-125.

Moore et al., "The future is now: neuroprotection during cardiopulmonary resuscitation," Current Opinion in Critical Care, Jun. 1, 2017, 23(3):215-222, abstract.

Morganti-Kossman et al., "Cytokines in the Brain: Production of cytokines following brain injury: beneficial and deleterious for the damaged tissue," Mol. Psychiatry, 1997, 2:133-136.

Nakka et al., "Endoplasmic Reticulum Stress Plays Critical Role in Brain Damage After Cerebral Ischemia/Reperfusion in Rats," Neurotox. Res., 2010, 17:189-202.

Neumar et al., "Epinephrine and sodium bicarbonate during CPR following asphyxia cardiac arrest in rats," Resuscitation, 1995, 29:249-263.

Nguyen et al., "Early lactate clearance is associated with improved outcome in severe sepsis and septic shock," Crit. Care Med., 2004, 32:1637-1642.

Piel et al., "Metformin induces lactate production in peripheral blood mononuclear cells and platelets through specific mitochondrial complex I inhibition," Acta Physiol., 2015, 213:171-180.

Popp et al., "Cerebral Resuscitation: State of the Art, Experimental Approaches and Clinical Perspectives," Neurol. Clin., 2006, 24:73-87, vi.

Preissner et al., "Drug Cocktail Optimization in Chemotherapy of Cancer," PLoS One, Dec. 7, 2012, 7(12):e51020, 1-7.

Qin et al., "Edaravone improves survival and neurological outcomes after CPR in a ventricular fibrillation model of rats," American Journal of Emergency medicine, Jun. 29, 2016, 34(10):1944-1949.

Sabbah et al., "Chronic Therapy With Elamipretide (MTP-131), a Novel Motochondria-Targeting Peptide, Improves Left Ventricular and Mitochondrial Function in Dogs with Advanced Hearth Failure," Circ. Heart Fail., 2016, 9:e002206, 1-10.

Sharp et al., "Inhibition of the Mitochondrial Fission Protein Dynamin-Related Protein 1 Improves Survival in a Murine Cardiac Arrest Model," Crit. Care Med., Feb. 2015, 43(2):e38-e47.

Shoaib et al., "A Walk Through the Progression of Resuscitation Medicine, Special Issue: Surviving Cardiac Arrest," Ann. NY Acad. Sci., 2020, 1-14.

Shoaib et al., "Plasma metabolomics supports the use of long-duration cardiac arrest rodent model to study human disease by demonstrating similar metabolic alterations," Sci Rep., 2020, 10:19707, 14 pages.

Sikorska et al., "Derivatised alpha-tocopherol as a CoQ10 carrier in a novel water-soluble formulation," Biofactors, Jan. 1, 2003, 18(1-4):173-183.

Storm et al., "Good neurological outcome despite very low regional cerebral oxygen saturation during resuscitation—a prospective preclinical trial in 29 patients," Scand. J. Trauma Resusc. Emerg. Med., 2016, 24:43, 1-7.

Temple et al., "Predicting neurological outcome and survival after cardiac arrest," Continuing Education in Anaesthesia Critical Care & Pain, Dec. 2012, 12(6):283-287.

Trovero et al., "Evidence for a modulatory effect of sulbutiamine on glutamatergic and dopaminergic corticol transmissions in the rat brain," Neurosci. Lett., 2000, 292:49-53.

Tsai et al., "Combination of Intravenous Ascorbic Acid Administration and Hypothermia After Resuscitation Improves Myocardial Function and Survival in a Ventricular Fibrillation Cardiac Arrest Model in the Rat," Acad. Emerg. Med., 2014, 21:257-265.

Vereczki et al., "Normoxic resuscitation after cardiac arrest protects against hippocampal oxidative stress, metabolic dysfunction, and neuronal death, J. Cereb. Blood Flow Metab., 2006, 26:821-835.

Walters et al., "Poloxamer-188 Reduces Muscular Edema After Tourniquet-Induced Ischemia-Reperfusion Injury in Rats," J. Trauma Inf. Inf. Crit. Care, May 2011, 70(5):1192-1197.

Weinreich et al., "REGN-COV2, a Neutralizing Antibody Cocktail, in Outpatients with Covid-19," N, Engl. J. Med., (online Dec. 17, 2020), 2021, 384:238-251.

(56) References Cited

OTHER PUBLICATIONS

Xiang et al., "Inflammatory mechanisms involved in brain injury following cardiac arrest and cardiopulmonary resuscitation (Review)," Biomed. Rep., 2016, 5:11-17.

Xu et al., "Inhibiting High-Mobility Group Box 1 (HMGB1) Attenuates Inflammatory Cytokine Expression and Neurological Deficit in Ischemic Brain Injury Following Cardiac Arrest in Rats," Inflammation, Aug. 2016, 39(4):1594-1602.

Yin et al., "Increasing expression of (CCAAT enhancer binding protein) homologous protein induced by endoplasmic reticulum stress in myocardium after cardiac arrest and resuscitation in rat," Resuscitation, 2012, 83:378-385.

Zhang et al., "Increased Survival Time With SS-31 After Prolonged Cardiac Arrest in Rats," Heart Lung Circ., 2019, 28:505-508.

Zhang et al., "Neuroprotective Effect of the Inhibitor Salubrinal after Cardiac Arrest in a Rodent Model," Oxid. Med. Cell Longev., 2020, 7468738, 1-9.

Zheng et al., "Sudden Cardiac Death in the United States, 1989 to 1998," Circulation, 2001, 104(18):2158-2163. doi:10.1161/hc4301.098254. PMID 11684624.

Zhu et al., "Metformin Improves Neurologic Outcome Via AMP-Activated Protein Kinase-Mediated Autophagy Activation in a Rat Model of Cardiac Arrest and Resuscitation," J. Am. Heart Assoc., 2018, 7:e008389, 1-19.

\* cited by examiner

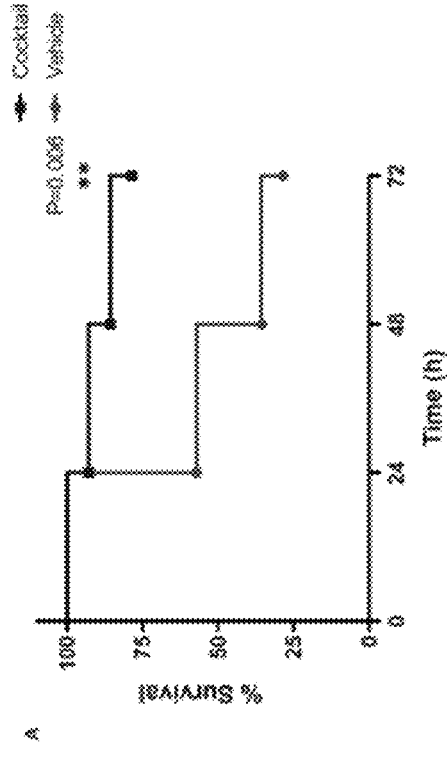
FIG. 8A
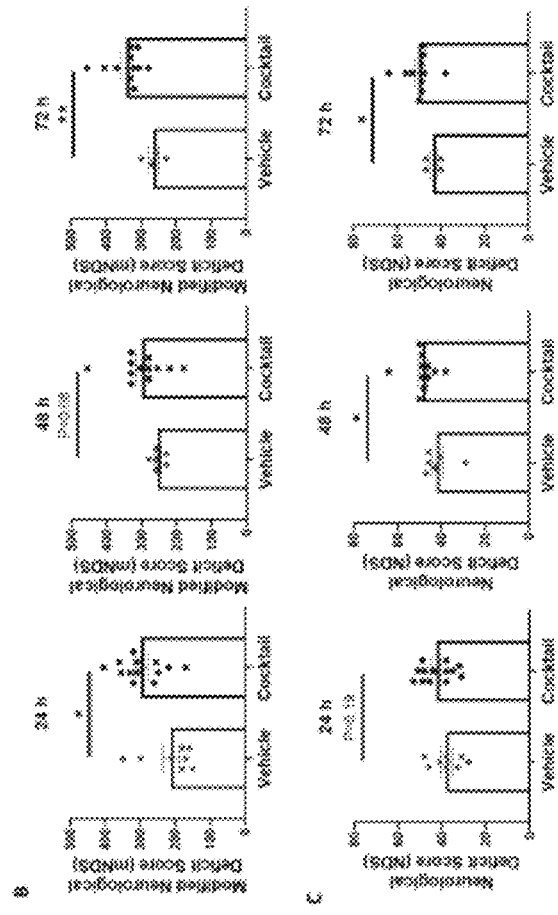
FIG. 8B
FIG. 8C

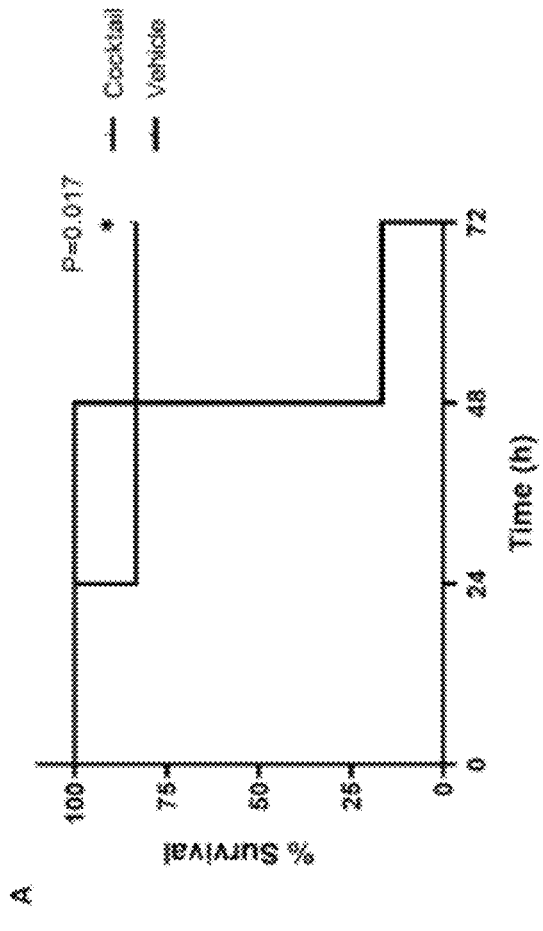
FIG. 11A
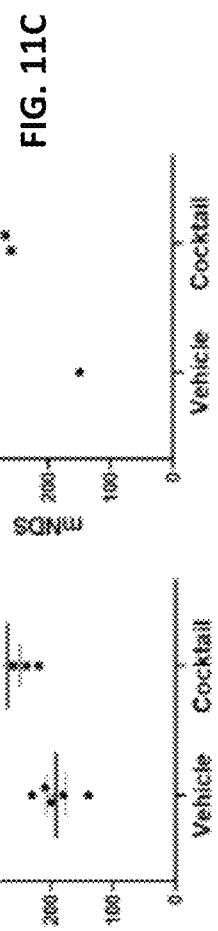
FIG. 11B
FIG. 11C

METHODS AND COMPOSITIONS FOR NEUROPROTECTION

The present application claim priority to U.S. provisional application No. 63/114,786 filed Nov. 17, 2020, which incorporated herein by reference in its entirety.

FIELD

The present disclosure relates to compositions, methods of preparation of the compositions, and methods including administration of said compositions for the prevention of neurological damage associated with cerebral ischemia.

BACKGROUND

Cardiac arrest accounts for about 15% of all deaths in Western countries.[25] In the United States 326,000 cases of out of hospital and 209,000 cases of in hospital cardiac arrest occur among adults a year.[26],[27] In the United States, during pregnancy cardiac arrest occurs in about one in twelve thousand deliveries or 1.8 per 10,000 live births.

Cardiac arrest is a devastating event. Despite improving resuscitation practices, mortality for those who suffer an out-of-hospital cardiac arrest (OHCA) is >90% with many survivors being left with severe neurological impairment. The primary injury occurs at the time of arrest and is non-reversible, and the secondary injury follows return of spontaneous circulation (ROSC) and subsequent cerebral reperfusion and is potentially reversible. The brain is exquisitely sensitive to hypoxia. Within 20 s of circulatory arrest, neuronal oxygen stores are used up leading to unconsciousness. After 5 min, glucose and adenosine triphosphate (ATP) stores are depleted. This leads to disruption in calcium homeostasis, free radical formation, and the activation of harmful protease cascades and cell death signaling mechanisms. This causes the primary cerebral injury.[28] Injury may also result from cerebral reperfusion after cardiac arrest.

There is a need for treatments to offer neuroprotection against the devastating effects of cerebral ischemia and cerebral hypoxia caused by cardiac arrest and other conditions which reduce blood flow to the brain. The present disclosure satisfies this need.

SUMMARY

In one aspect, a method of providing neuroprotection to a brain of a subject suffering from, having suffered from, or at risk of suffering from, cerebral ischemia, comprising co-administering to the subject an effective amount of at least two therapeutic agents selected from the group consisting of a mitochondrial complex-1 inhibitor, antioxidant, lipid bilayer stabilizer, mitochondrial permeability transition pore inhibitor, mitochondrial membrane protection agent, thiamine supplementing agent, and NHE-1 inhibitor.

In some embodiments, an effective amount of one or more of the following therapeutic agents is co-administered to the subject: metformin, N-acetyl cysteine, vitamin C, edaravone, polaxamer 188, SS-31, CoQ10, cyclosporine A, sulbutiamine or a derivative thereof, and zoniporide, or pharmaceutically acceptable salts of any thereof.

In some embodiments, the cerebral ischemia comprises or is caused by diffuse cerebral hypoxia (DCH), focal cerebral ischemia, cerebral infarction, ischemia-reperfusion, sickle cell anemia, atherosclerosis, blood vessel compression, ventricular tachycardia, blood clot, low blood pressure, cardiac arrest, congenital heart defect, cardiac conduction defect, and global cerebral ischemia. In some embodiments, the cerebral ischemia comprises cerebral hypoxia caused by cardiac arrest, asthma, anemia, drowning, choking, stroke, carbon monoxide poisoning, opioid overdose, CNS-depressant overdose, status epilepticus, exposure to nitrogen-rich environments, ascent from a water dive, shallow water blackout, flying at altitude in an unpressurized cabin, and physical exertion at high altitudes.

In another aspect, a pharmaceutical composition for providing neuroprotection to a brain of a subject suffering from, having suffered from, or at risk of suffering from, cerebral ischemia is provided, the composition comprising an effective amount of at least two therapeutic agents disclosed herein.

In another aspect, a method of preparing a pharmaceutical composition for providing neuroprotection to a brain of a subject suffering from, having suffered from, or at risk of suffering from, cerebral ischemia is provided, the method comprising mixing:
  a) a first mixture comprising CoQ10 and cyclosporin A; and
  b) a second mixture comprising metformin, N-acetyl cysteine, polaxamer-188, edaravone, SS-31, vitamin C, and zoniporide;
to form a third mixture. In some embodiments, the method further comprises mixing with the third mixture a fourth mixture comprising sulbutiamine or a derivative thereof.

BRIEF DESCRIPTION OF THE DRAWINGS

(FIG. 5A) esophageal temperature (° C.) (FIG. 5B) mean arterial pressure (MAP) (FIG. 5C) heart rate (HR). *-p<0.05 Vs Vehicle; **-p<0.005 Vs Vehicle; #-p<0.05 Vs respective baseline; ### p<0.0005 Vs respective baseline; ###-p<0.0001 Vs respective baseline; Bars represent the mean and SEM. T eso, esophageal temperature; BL indicates baseline; CPR, cardiopulmonary resuscitation. *=p<0.05, **=p<0.005.

FIG. 8A-8C: Cocktail improves survival and neurological function after asphyxial cardiac arrest and resuscitation. FIG. 8A, Survival substantially differed between vehicle-treated (28.6%) and cocktail-treated (78.6%) rats at 72 h after return of spontaneous circulation (ROSC; P=0.006). FIG. 8B, Modified neurological deficit score (mNDS; Scale 1) at 24, 48, and 72 h in vehicle-treated and cocktail-treated rats. Rats who did not survive (score=0) were excluded from the statistical analysis. FIG. 8C, Neurological deficit score (NDS; Scale 2) in vehicle-treated and cocktail-treated rats at 24, 48, and 72 h post-ROSC. Scores significantly differed at 24 and 72 h post-ROSC, but not at 48 h (although they showed an increasing trend). Data are presented as mean±SEM. *P<0.05, **P<0.005.

FIGS. 9A and 9B, Representative (FIG. 9A) Nissl and (FIG. 9B) TUNEL staining showing reduced apoptotic cells in hippocampus of cocktail-treated rats. Blue box indicates the CA1 region and red box indicates the CA3 region of the hippocampus in the left cerebral hemisphere. Red arrows indicate ischemic neurons, and orange arrows indicate apoptotic cells. The average number of ischemic neurons and apoptotic cells in the CA1 and CA3 regions of the hippocampus were significantly greater in vehicle-treated rats than sham rats, and they were significantly reduced in cocktail-treated rats versus vehicle-treated rats. Data are presented as mean±SEM. *P<0.05, P<0.01, *P<0.001, and ****P<0.0001.

FIG. 10A, Lactate concentration was significantly higher at 20 and 40 min after return of spontaneous circulation (ROSC) versus baseline (BL) in both vehicle-treated and cocktail-treated rats. Lactate concentration was greater in cocktail-treated rats versus vehicle-treated rats at 20 and 40 min post-ROSC. FIG. 10B, Glucose concentration was higher in cocktail-treated rats than vehicle-treated rats, with the most significant difference at 20 min post-ROSC (P<0.05). Glucose concentration showed a decreasing trend in both groups over the experimental time course. FIG. 10C, Mean arterial pressure (MAP) was significantly greater in vehicle-treated rats versus cocktail-treated rats only at 30 min post-ROSC. FIG. 10D, Heart rate (HR) in beats per minute (bpm) was significantly higher in vehicle-treated rats versus cocktail-treated rats only at 60 min post-ROSC (D). Data are presented as mean±SEM, and significant comparisons intragroup are shown in the inserts. *P<0.05, **P<0.01 between vehicle and cocktail.

FIG. 11A-11C. Preliminary study of survival and neurological deficit in cocktail-treated and vehicle-treated rats after cardiac arrest. FIG. 11A, Survival analysis of cocktail-treated and vehicle-treated rats after 12 min cardiac arrest (CA) and resuscitation in the preliminary study. Survival was substantially greater in cocktail-treated rats at 72 h post-ROSC. FIGS. 11B and 11C, Modified neurological deficit score (mNDS) at (FIG. 11B) 24 and (FIG. 11C) 48 h of vehicle-treated and cocktail-treated rats after 12 min CA and resuscitation in the preliminary study. Rats who did not survive (score=0) were excluded from the statistical analysis. Scores in cocktail-treated rats were significantly higher than vehicle-treated rats at 24 h after return of spontaneous circulation (ROSC). Only 1 vehicle-treated rat survived at 48 h post-ROSC. Data are presented as mean±SEM. *P<0.05 between vehicle and cocktail.

DETAILED DESCRIPTION

Figure 1:
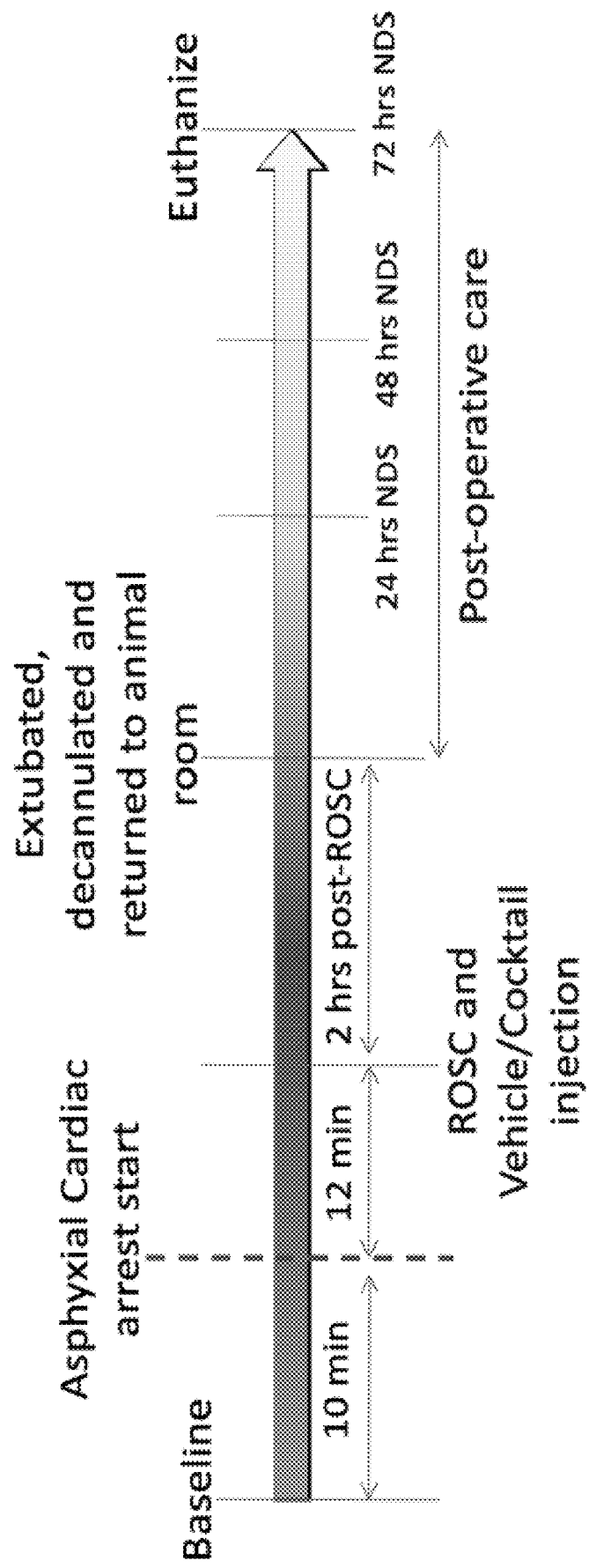
FIG. 1: shows a diagram representing experimental time detail of the experiment of Example 1 wherein cardiac arrest (CA) was initiated in rats followed by administration of the formulation according to the present invention.

The practice of the present disclosure will employ, unless otherwise indicated, conventional methods of chemistry, biochemistry, and pharmacology, within the skill of the art. Such techniques are explained fully in the literature. See, e.g.; A. L. Lehninger, Biochemistry (Worth Publishers, Inc., current addition); Morrison and Boyd, Organic Chemistry (Allyn and Bacon, Inc., current addition); J. March, Advanced Organic Chemistry (McGraw Hill, current addition); Remington: The Science and Practice of Pharmacy, A. Gennaro, Ed., 20th Ed.; FDA's Orange Book, Goodman & Gilman The Pharmacological Basis of Therapeutics, J. Griffith Hardman, L. L. Limbird, A. Gilman, 11th Ed., 2005, The Merck Manual, 18th edition, 2007, and The Merck Manual of Medical Information 2003.

As used herein and in the claims, the singular forms "a," "an," and "the" include the plural reference unless the context clearly indicates otherwise. Throughout this specification, unless otherwise indicated, "comprise," "comprises" and "comprising" are used inclusively rather than exclusively. The term "or" is inclusive unless modified, for example, by "either." Thus, unless context or an express statement indicates otherwise, the word "or" means any one member of a particular list and also includes any combination of members of that list. Other than in the examples, or where otherwise indicated, all numbers expressing quantities of ingredients or reaction conditions used herein should be understood as modified in all instances by the term "about."

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

When an embodiment is defined by one of these terms (e.g., "comprising") it should be understood that this disclosure also includes alternative embodiments, such as "consisting essentially of" and "consisting of" for said embodiment.

"Substantially" or "essentially" means nearly totally or completely, for instance, 95%, 96%, 97%, 98%, 99%, or greater of some given quantity.

"Pharmaceutically acceptable excipient or carrier" refers to an excipient that may optionally be included in the compositions of the disclosure and that causes no significant adverse toxicological effects to the patient.

"Pharmaceutically acceptable salt" refers to salts of a compound, which salts are suitable for pharmaceutical use and are derived from a variety of organic and inorganic counter ions well known in the art. Pharmaceutically acceptable salts include, when the compound contains an acidic functionality, by way of example only, sodium, potassium, calcium, magnesium, ammonium, and tetraalkylammonium. When the molecule contains a basic functionality, salts of organic or inorganic acids, such as hydrochloride, hydrobromide, tartrate, mesylate, acetate, maleate, and oxalate. Stahl and Wermuth, eds., "Handbook of Pharmaceutically Acceptable Salts," (2002), Verlag Helvetica Chimica Acta, Zurich, Switzerland), which is hereby incorporated by reference for its teachings related to pharmaceutically acceptable salts, discusses a variety of pharmaceutical salts, their selection, preparation, and use. Pharmaceutically acceptable salts also include salts formed when an acidic proton present in the parent compound is either replaced by a metal ion (e.g., an alkali metal ion, an alkaline earth metal ion, or an aluminum ion) or by an ammonium ion (e.g., an ammonium ion derived from an organic base, such as, ethanolamine, diethanolamine, triethanolamine, morpholine, piperidine, dimethylamine, diethylamine, triethylamine, and ammonia).

The terms "subject," "individual" or "patient" are used interchangeably herein and refer to a vertebrate, preferably a mammal. Mammals include, but are not limited to, mice, rodents, rats, simians, humans, farm animals, dogs, cats, sport animals, and pets.

The terms "pharmacologically effective amount" or "therapeutically effective amount" or "effective amount" of a composition or agent, as provided herein, refer to a nontoxic but sufficient amount of the composition or agent to provide the desired response, such as a reduction or reversal of progressive neurodegenerative diseases. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

The term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term. For example, in some embodiments, it will mean plus or minus 5% of the particular term. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the disclosure.

Headings are provided for convenience only and are not to be construed to limit the invention in any way. Unless defined otherwise, all technical and scientific terms used herein have the same meaning as those commonly understood to one of ordinary skill in the art. The terminology used herein is for the purpose of describing particular embodiments only and is not intended to limit the scope of the present invention, which is defined solely by the claims. It also is to be understood, although not always explicitly stated, that the reagents described herein are merely exemplary and that equivalents of such are known in the art and are set forth throughout the detailed description.

As used herein, the term "treatment" or "treating" means any treatment of a disease or condition or associated disorder, in a patient, including:

Inhibiting or preventing the disease or condition, that is, arresting or suppressing the development of clinical symptoms, such as neurological deficits resulting from cerebral ischemia, also included within "treatment" is provision of neuroprotection; and/or relieving the disease or condition that is, causing the regression of clinical symptoms, e.g., increasing neurological performance or reducing neurological defects.

In some embodiments, "treatment" encompasses "providing neuroprotection" to the subject. "Treatment" and "providing neuroprotection" may comprise the administration of the therapeutics agent(s) or compositions disclosed herein.

"Neuroprotection" refers to the relative preservation of neuronal structure and/or function. In the case of an ongoing insult (a neurodegenerative insult such as cerebral hypoxia) the relative preservation of neuronal integrity implies a reduction in the rate of neuronal loss over time.

"Cerebral hypoxia" is a form of hypoxia (reduced supply of oxygen), specifically involving the brain; when the brain is completely deprived of oxygen, it is called cerebral anoxia.

"Cerebral ischemia," as used herein, refers to reduction of or insufficient blood flow to the brain, relative to a healthy subject.

"Cardiac arrest" refers to a sudden loss of blood flow resulting from the failure of the heart to pump effectively. Signs include loss of consciousness and abnormal or absent breathing. Some individuals may experience chest pain, shortness of breath, or nausea before cardiac arrest.

"Composition" and "formulation" are used herein interchangeably. These terms refer to a mixture of one or more therapeutic agents and a carrier, excipient, or other inactive ingredients.

"Mitochondrial complex 1" as used herein, refers to respiratory complex I, NADH:ubiquinone oxidoreductase, or type I NADH dehydrogenase. It is the first large protein complex of the respiratory chains of many organisms from bacteria to humans. It catalyzes the transfer of electrons from NADH to coenzyme Q10 (CoQ10) and translocates protons across the inner mitochondrial membrane in eukaryotes.

"Antioxidant" as used herein, refers to compounds that inhibit oxidation. Oxidation is a chemical reaction that can produce free radicals, thereby leading to chain reactions that may damage the cells of organisms.

"Lipid bilayer stabilizer," as used herein, comprises any agent that stabilizes the lipid bilayer of a biological organism. Lipid bilayer stabilizers serve to decrease Blood-Brain Barrier damage, reduce brain edema and reduce cellular death.

"Mitochondrial permeability transition pore" or "MTP," as used herein, refers to a protein that is formed in the inner membrane of the mitochondria under certain pathological conditions such as traumatic brain injury and stroke. Opening allows increase in the permeability of the mitochondrial membranes to molecules of less than 1500 Daltons in molecular weight. Induction of the permeability transition pore, mitochondrial membrane permeability transition (mPT or MPT), can lead to mitochondrial swelling and cell death through apoptosis or necrosis. An inhibitor of MTP enhances mitochondrial transmembrane potential promoting cytochrome C release from mitochondria and increases superoxide dismutase activity to provide neuroprotection "Mitochondrial membrane protection agent," as used herein, refers to any agent that interacts with cardiolipin and protects mitochondria membranes and protects against mitochondrial damage.

"Thiamine supplementing agent," as used herein, refers to any agent that releases, metabolizes into, or has related pharmacological activity of thiamine.

"NHE-1," as used herein, refers to the sodium-hydrogen antiporter 1 (NHE-1) also known as sodium/hydrogen exchanger 1 or SLC9A1 (SoLute Carrier family 9A1). NHE-1 is an isoform of sodium-hydrogen antiporter that in humans is encoded by the SLC9A1 gene. It is a ubiquitous membrane-bound enzyme involved in volume- and pH-regulation of vertebrate cells.

"Metformin," as used herein refers to the compound:

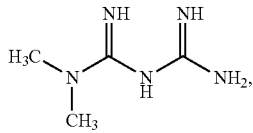

and pharmaceutically acceptable salts or solvates thereof. The compound is also marketed as Glucophage®.

"N-acetyl cysteine" (NAC) refers to the compound:

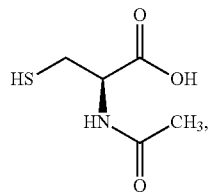

or a pharmaceutically acceptable salt or solvate thereof.

"Vitamin C" as used herein, refers to the compound ascorbic acid or a pharmaceutically acceptable salt or solvate thereof.

"Edaravone," as used herein, refers to the compound of structure:

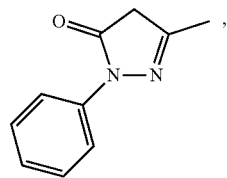

or a pharmaceutically acceptable salt or solvant thereof. Edaravone is marketed as Radicut®, Radicava®, Xavron®, or Edavit®.

"Polaxamer 188," as used herein refers to a block copolymer of structure:

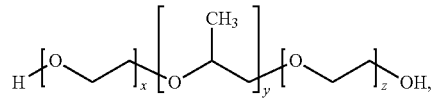

wherein x may be 2-130, y may be 15-67 and z may be 2-130, and the total average molecular weight is about 8,400 Da.

"SS-31," also known as elamipretide, refers to a compound of structure:

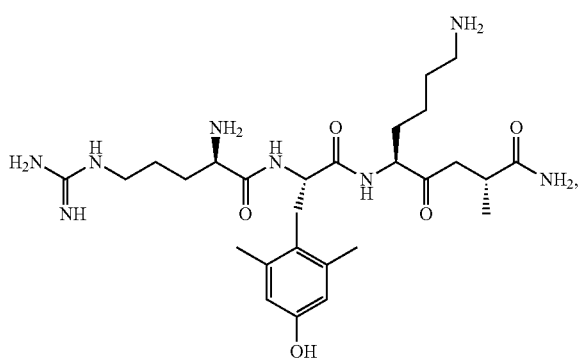 [SMILES: Cc1cc(O)cc(C)c1C[C@H](NC(=O)[C@H](N)CCCNC(=N)N)C(=O)N[C@@H](CCCCN)C(=O)C[C@@H](C)C(N)=O]

or a pharmaceutically acceptable salt or solvate thereof.

"Coenzyme Q10," or "CoQ10" also known as ubiquinone-10, is a coenzyme member of a family of CoQs that are ubiquitous in animals and most bacteria. In humans, the most common form of CoQ is CoenzymeQ10 having the structure:

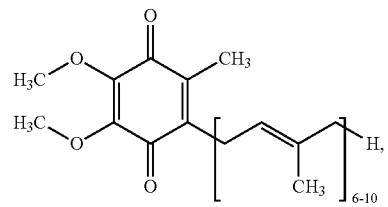

"Cyclosporin A" refers to an immunosuppressive compound of formula:

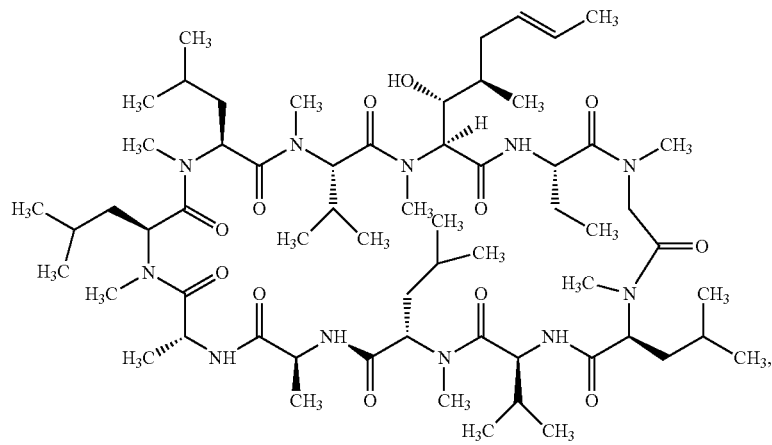

or a pharmaceutically acceptable salt or solvate thereof.

"Sulbutiamine" (Arcalion®) refers to a synthetic derivative of thiamine (vitamin B1) of structure:

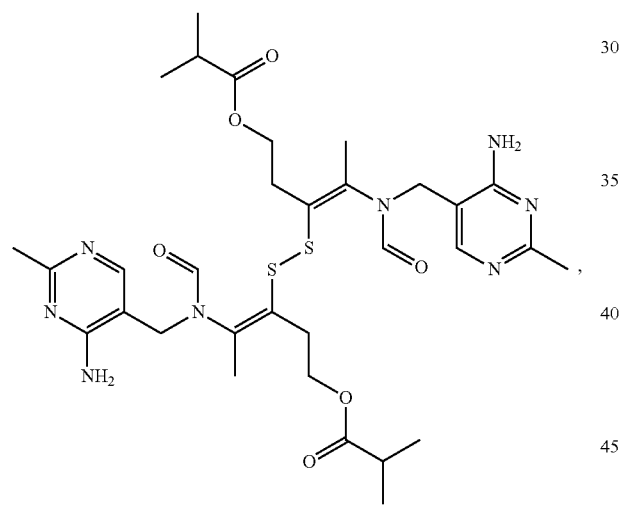

or a pharmaceutically acceptable salt or solvate thereof. Derivatives of sulbutiamine can also be used. For example, the following compound has been synthesized from sulbutiamine and is suitable for use in the present compositions:

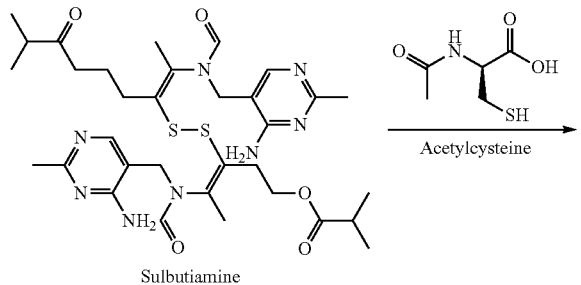
Sulbutiamine

-continued

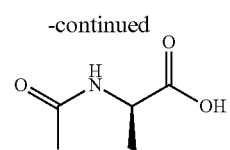

Conjugated product (M659)
Exact Mass: 513.17

"Zoniporide," as used herein refers to the compound:

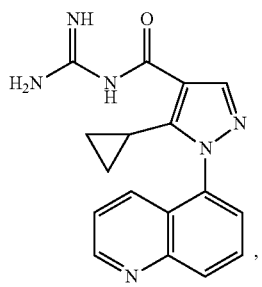 [SMILES: N=C(N)NC(=O)c1cnn(-c2cccc3ncccc23)c1C1CC1]

or a pharmaceutically acceptable salt or solvate thereof.

Methods of Providing Neuroprotection

In one aspect, a method of providing neuroprotection to a brain of a subject suffering from, having suffered from, or at risk of suffering from, cerebral ischemia is provided, the method comprising co-administering to the subject an effective amount of at least two therapeutic agents selected from the group consisting of a mitochondrial complex-1 inhibitor, antioxidant, lipid bilayer stabilizer, mitochondrial permeability transition pore inhibitor, mitochondrial membrane protection agent, thiamine supplementing agent, and NHE-1 inhibitor.

In an embodiment, neuroprotection comprises preserving neuronal structure and/or function. Preservation of neuronal structure may be assessed using tools such as imaging techniques such as magnetic resonance imaging (MRI), functional MRI (fMRI), Positron Emission Tomography (PET), and Electroencephalography (EEG). Preservation of neuronal function may be assessed using any clinically relevant test known in the art, for example, ear opening and eye opening, surface righting, air righting, forelimb grasp, auditory startle, surface righting, negative geotaxis, open field traversal, cliff aversion, Barnes maze, elevated plus maze, Jamar dynamometer, handheld dynamometry, manual muscle testing (MMT), isokinetic dynamometry, trunk stability test (TST), unilateral hip bridge endurance test (UHBE), pronator sign, Barré sign, Romberg test, Landau reflex, particle suspension, sensory reflex (pinprick, light touch, position, vibration, and charger), reflex (biceps, triceps, brachioradialis, patellar, and ankle), Moro reflex, tonic neck response, sucking reflex, palmer and planter grasp reflex, parachute response, neck on body righting reaction (NOB), body on body righting reaction (BOB), ear opening auditory reflex, static compliance, physical volume of ear canal, contralateral reflex, ipsilateral reflex, tympanometry, Y-maze, Novel Object Recognition Task, STPI (State-Trait Personality Inventory), the Five Dimensional Curiosity Scale, Self Curiosity Attitude Interests Scale, Curiosity and Exploration Inventory-II, State-Trait Personality Inventory (STPI), subscales of the Sensation Seeking Scale (SSS), Bayley Scales of Infant Development (BSID-III) (1-42 months), the Mullen Scales of Early Learning (1-68 months), the Fagan Test of Infant Intelligence (FTII) (Birth-12 months), Griffith's Mental Development Scales I (0-2 years), Battelle Developmental Inventory (BDI) (Birth-8 years), and the Vineland Adaptive Behaviour Scale (0-18 years) or cognition tests including ADASCog, Mini-Mental State Exam (MMSE), Mini-cog test, Woodcock-Johnson Tests of Cognitive Abilities, Leiter International Performance Scale, Miller Analogies Test, Raven's Progressive Matrices, Wonderlic Personnel Test, IQ tests, and a computerized tested selected from Cantab Mobile, Cognigram, Cognivue, Cognision, or Automated Neuropsychological Assessment Metrics Cognitive Performance Test (CPT).

In some embodiments, the extent of neuroprotection provided by the method or composition may be determined by assessing the subject using any tool described above to assess neuronal structure and/or function, and comparing the subject's results to a control subject(s) of the same age, sex and species that has not experienced cerebral ischemia. In some embodiments, after cerebral ischemia and co-administration, the subject scores about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% of what the control subject scores on any of the aforementioned tools or tests listed above for assessment of neuronal structure and/or function.

In some embodiments the cerebral ischemia comprises reduced blood flow to the brain. In some embodiments the cerebral ischemia comprises ischemic cerebral hypoxia (oxygen deprivation due to a disruption in blood flow). The reduction in blood flow to the brain and/or cerebral hypoxia may be caused by one or more of cardiac arrest, asthma, anemia, drowning, choking, stroke, carbon monoxide poisoning, opioid overdose, CNS-depressant overdose, status epilepticus, exposure to nitrogen-rich environments, blood clot, atherosclerosis, ascent from a water dive, shallow-water blackout, flying at altitude in an unpressurized cabin, and physical exertion at high altitudes.

Cerebral hypoxia or cerebral ischemia may be determined to exist in a subject by arterial blood gas or ABG test, MRI of the brain, computed tomography (CT) scan of the brain, echocardiogram, electrocardiogram, electroencephalogram, cerebral angiography, carotid duplex, Doppler ultrasound, magnetic resonance angiogram, examination of skin color (pale skin), examination of lip color (blue lips indicated hypoxia), unconsciousness in the subject, reduction from normal respiratory rate (12-20 breaths per minute) in the subject.

In some embodiments, the co-administration is to a subject displaying or having displayed one or more symptoms selected from the group consisting of dizziness, nausea, or vomiting, unusually severe headache, confusion, disorientation or memory loss, numbness or weakness in an extremity or face, abnormal or slurred speech, difficulty with comprehension, loss of vision or difficulty seeing, loss of balance, coordination or the ability to walk, pale skin, blue lips, unconsciousness, pinpoint pupils, dilated pupils, labored breathing, tachycardia, bradycardia, cessation of pulse, cessation of respiration, reduced pulse relative to resting heart rate, and reduced respiration rate relative to resting rate of respiration.

In some embodiments, the co-administration of the at least two therapeutic agents comprises sequential administration. In some embodiments, the co-administration of the at least two therapeutic agents comprises concurrent administration. In embodiments comprising co-administration of three or more therapeutic agents, any two or more therapeutic agents may be administered concurrently, while the remaining therapeutic agent(s) are administered sequentially relative to the concurrently administered agents. Any of the remaining therapeutic sequentially administered relative to the concurrently administered agents, may themselves be administered sequentially or concurrently relative to each other.

In some embodiments administration of one or more of the therapeutic agents co-administered comprises intravenous, intramuscular, intracardiac, subcutaneous, oral, sublingual, buccal, intranasal, rectal, vaginal, and transdermal administration.

In some embodiments, the administration of one or more agents co-administered is via an implanted pump in the subject. The implanted pump may be configured with a pacemaker of the subject to administer therapeutic agent(s) during or after cardiac arrest.

In some embodiments, the co-administration comprises administration of two therapeutic agents to the subject. In some embodiments, the co-administration is comprises administration of three therapeutic agents to the subject. In some embodiments, the co-administration comprises administration of four therapeutic agents to the subject. In some embodiments, the co-administration is comprises administration of 5, 6, 7, 8, 9, 10, 11, 12, 13, 14, 15, 16, 17, 18, 19, 20, 21, 22, 23, 24, or 25 therapeutic agents to the subject. In some embodiments, the at least two therapeutics agents may be administered to the subject concurrently.

In some embodiments, the mitochondrial complex 1 inhibitor comprises one or more of rotenone, metformin, buformin, phenformin, galegine, synthalin A, piericidin, capsaicin, rolliniastatin, stigmatellin, mucidin, coenzyme Q2, JCI-20679, celastrol, AG311, kalkitoxin, BAY 87-2243, xanthohumol, verrucosidin, canagliflozin, fenofibrate, deguelin, RTC1, RTB70, cycloguanil, proguanil, amilorides (EIPA, MIA, and benzamil), acaricides (fenazaquin, fenpyroximate, pyridaben, and tebufenpyrad), nafuredin, A-769662, salicylate bullatacin, piericidin, acetogenins, adenosine diphosphate ribose, Analogue 13, ubicidin3, hydroxypyridine analogue 3, otivarin, phenoxan, thiangazole, myxalamid PI, phenalamid $A_2$, aurachin A, myxothiazol, TDS, aureothin, cochlioquinone B, pterulone, analogue 37, rhein, papaverine, ubiquinone2, ubiquinone3, idebenone, Sandoz 547A, pyridaben, fenpyroximate, tebufenpyrad, fenazaquin, benzimidazole, cyhalothrin, 6-chlorobenzothiadiazole, 2M-TIO, amytal, meperedine (Demerol®), meperidine analogue49, $MPP^+$, decyl-$MPP^+$, MQ18, 2-methyltharmine, TIQ, aminoethyl cysteineketamine, haloperidol, $HPP^+$, dequalinium chloride, cinnarizine, ranolazine, vacor, nonyl-phenol, catechol, dinitrophenol, CCCP, 4-s-butyl analogue, 7-chloro-4-octyloxy analogue, 2-undecyl-3-methyl analogue, 4-hydroxy analogue 37, 4'-hepatyl analogue, erythrosine 5'iodoacetamide, safranine, di005(3) (D-272), diOC6(3), DPI, DCCD, o-phenantroline, and MitoSNO.

In some embodiments, the antioxidant comprises one or more of thiols, ascorbic acid (vitamin C), glutathione, catalase enzymes, superoxide dismutase enzyme, vitamin E and derivatives thereof, uric acid, ubiquinone, selenium, zinc, lipoic acid, carotenes, tocopherols, ubiquinol, peroxiredoxins, propyl gallate (PG, E310), tertiary butylhydroquinone (TBHQ), butylated hydroxyanisole (BHA, E320), butylated hydroxytoluene (BHT, E321), *allium* sulphur compounds, anthocyanins, beta-carotene, catechins, copper, cryptoxanthins, flavonoids, indoles, isoflavonoids, lignans, lutein, lycopene, manganese, vitamin A, zoochemicals, ubiquinol-10, N-acetyl cysteine, zinc, selenium, copper, quercetin, myricetin, apigenin, taxifolin, luteoline, epigallocatechin, hesperetin, naringenin, cynidin, delphidin, genistein, daidzein, ferulic acid, caffeic acid, sinapic acid, p-coumaric acid, theaflavin, theafavin-3-gallate, allicin, piperine, curcumin, allium sulphur compounds, polyphenols, deferoxamine cortisone, estradiol, estriol, melatonin and oestrogen.

In some embodiments, the lipid bilayer stabilizer comprises one or more of poloxamer 188, polaxamer 407, kolliphor P188, Pluronic F-127, Triton X-100, Brij 93, poly(ethylene glycol)-block-poly(propylene glycol)-block-poly(ethylene glycol) (with a molecular weight selected from 500-100 Da, 1000-2000 Da, 2000-3000 Da, 3000-4000 Da, 4000-5000 Da, 5000-6000 Da, 6000-7000 Da, 7000-8000 Da, 8000-9000 Da, 9000-11000 Da, 11000-13000 Da or greater than 13000 Da), Pluronic F68, Flocor and RheothRx, and SPAN 80, docosahexaenoic acid (DHA).

In some embodiments, the mitochondrial permeability transition pore inhibitor comprises one or more of cyclosporin A, sanglifehrin A, FLOCOR, NIM-811, Kolliphor® P 188, ER-000444793, pluronic F68 Decylubiquinone (55486-00-5), GNX-4728, GNX-4975, AntiOxBEN3, TR040303 and TRO 19622.

In some embodiments, the mitochondrial membrane protection agent comprises SS-31.

In some embodiments, the thiamine supplementing agent comprises sulbutiamine, thiamine, and other nootropic drugs such as modafinil (Provigil®), amphetamine (Adderall®), methamphetamine (Desoxyn®), methylphenidate (Ritalin®), and memantine (Axura®).

In some embodiments, the NHE-1 inhibitor comprises one or more of zoniporide, cariporide, amiloride, eniporide, cariporide, rimeporide, Phx-3 (2-aminophenoxazine-3-one), 9t (5-aryl-4-(4-(5-methyl-1H-imidazol-4-yl)piperididn-1-yl), a BIX NHE1 inhibitor, KR-32568, empagliflozin (EMPA), sabiporide, dapagliflozin (DAPA), canagliflozin (*CANA*) and amiloride.

In some embodiments, an effective amount of one or more of the following therapeutic agents: metformin, N-acetyl cysteine, vitamin C, edaravone, polaxamer 188, SS-31, CoQ10, cyclosporin A, sulbutiamine, and zoniporide is administered to the subject concurrently in a separate composition. In some embodiments, at least two of the following therapeutic agents are mixed together in a single composition and then administered as a single or multiple compositions: metformin, N-acetyl cysteine, vitamin C, edaravone, polaxamer 188, SS-31, CoQ10, cyclosporin A, sulbutiamine, and zoniporide.

In some embodiments, the co-administration may involve administering to the subject a pharmaceutical composition prepared or obtained by mixing an effective amount of each of the following therapeutic agents: metformin, N-acetyl cysteine, vitamin C, edaravone, polaxamer 188, SS-31, CoQ10, cyclosporin A, sulbutiamine, and zoniporide.

In some embodiments, the effective amount of any therapeutic agent co-administered, in milligrams per kg of subject mass, is selected from:
 metformin: about 80 mg/kg to about 120 mg/kg;
 N-acetyl cysteine: about 120 mg/kg to about 180 mg/kg;
 poloxamer 188: about 120 mg/kg to about 180 mg/kg;
 CoQ10: about 24 mg/kg to about 36 mg/kg;
 cyclosporin A: about 8 mg/kg to about 12 mg/kg;
 edaravone: about 2.4 mg/kg to about 3.6 mg/kg;
 SS-31: about 0.4 mg/kg to about 0.6 mg/kg;
 sulbutiamine: about 10 mg/kg to about 15 mg/kg;
 vitamin C: about 80 mg/kg to about 120 mg/kg; and
 zoniporide: about 2.4 mg/kg to about 3.6 mg/kg.

In some embodiments, the effective amount of any therapeutic agent co-administered, in milligrams per kg of subject mass, is selected from:
 metformin: about 100 mg/kg;
 N-acetyl cysteine: about 150 mg/kg;
 poloxamer 188: about 150 mg/kg;
 CoQ10: about 30 mg/kg;
 cyclosporin A: about 10 mg/kg;
 edaravone: about 3 mg/kg;
 SS-31: about 0.5 mg/kg;
 sulbutiamine: about 12.5 mg/kg;
 vitamin C: about 100 mg/kg; and
 zoniporide: about 3 mg/kg.

The cerebral ischemia may be caused by, include, or result in a condition selected from diffuse cerebral hypoxia (DCH), focal cerebral ischemia, cerebral infarction, ischemia-reperfusion, sickle cell anemia, atherosclerosis, blood vessel compression, ventricular tachycardia, blood clot, low blood pressure, cardiac arrest, congenital heart defect, cardiac conduction defect, global cerebral ischemia, asthma, anemia, drowning, choking, stroke, carbon monoxide poisoning, opioid overdose, CNS-depressant overdose, status epilepticus, exposure to nitrogen-rich environments, ascent from a water dive, shallow water blackout, flying at altitude in an unpressurized cabin, and physical exertion at high altitudes.

In some embodiments, the cerebral ischemia is caused by cardiac arrest, stroke, opioid overdose, CNS-depressant overdose, asthma attack, or loss of consciousness in the subject. The co-administration of the therapeutic agents to the subject may be about 30 seconds, about 1 min, about 2 min, about 3 min, about 4 min, about 5 min, about 10 min, about 15 min, about 20 min, about 25 min, about 30 min, about 35 min, about 40 min, about 45 min, about 50 min, about 55 min, about 60 min, about 65 min, about 70 min, about 75 min, about 80 min, about 85 min, or about 90 min after cardiac arrest, stroke, opioid overdose, CNS-depressant overdose, asthma attack, or loss of consciousness begins.

Co-administration of the therapeutic agents may precede the presence of cerebral ischemia. In some embodiments, the subject is at risk for cerebral ischemia and co-administration occurs 4× per day, 3× per day, 2× per day, daily, every other day, thrice per week, once a week or combinations thereof. The co-administration may continue for 1 day to about 1 week, about 1 week to about 2 weeks, about 2 weeks to about 4 weeks, about 4 weeks to about 2 months, about 2 months to about 6 months, about 6 months to about 1 year, or greater than about 1 year.

Pharmaceutical Compositions

In another aspect, a pharmaceutical formulation is provided for providing neuroprotection to a brain of a subject suffering from, having suffered from, or at risk of suffering from, cerebral ischemia. The composition may comprise an effective amount of at least two therapeutic agents selected from the group consisting of a mitochondrial complex-1 inhibitor, antioxidant, lipid bilayer stabilizer, mitochondrial permeability transition pore inhibitor, mitochondrial membrane protection agent, thiamine supplementing agent, and NHE-1 inhibitor. The composition may comprise one or more of the therapeutic agents of: metformin, N-acetyl cysteine, vitamin C, edaravone, polaxamer 188, SS-31, CoQ10, cyclosporin A, sulbutiamine, and zoniporide, or pharmaceutically acceptable salts of any thereof.

In some embodiments, wherein the therapeutic agents are in the formulation in a mass ratio of:
metformin:N-acetyl cysteine:poloxamer 188:coenzymeQ10 (CoQ10):cyclosporin A:edaravone:elamipretide (SS-31):sulbutiamine:vitamin C:zoniporide of
about 80 to about 120 (metformin):about 120 to about 180 (NAC):about 120 to about 180 (poloxamer 188):about 24 to about 36 (CoQ10):about 8 to about 12 (cyclosporin A):about 2.4 to about 3.6 (edaravone):about 0.4 to about 0.6 (SS-31):about 10 to about 15 (sulbutiamine):about 80 to about 120 (vitamin C):about 2.4 to about 3.6 (zoniporide),
wherein any one or more agents may be absent. For example a composition absent of metformin would comprise a ratio of:
N-acetyl cysteine:poloxamer 188:coenzymeQ10 (CoQ10):cyclosporin A:edaravone:elamipretide (SS-31):sulbutiamine:vitamin C:zoniporide of
about 120 to about 180:about 120 to about 180:about 24 to about 36:about 8 to about 12:about 2.4 to about 3.6:about 0.4 to about 0.6:about 10 to about 15:about 80 to about 120:about 2.4 to about 3.6.

In some embodiments, the therapeutic agents are in the formulation in a mass ratio of:
metformin:N-acetyl cysteine:poloxamer 188:coenzymeQ10 (CoQ10):cyclosporin A:edaravone:elamipretide (SS-31):sulbutiamine:vitamin C:zoniporide of
about 100:about 150:about 150:about 30:about 10:about 3:about 0.5:about 12.5:about 100:about 3, wherein any one or more agents may be absent.

In some embodiments, the pharmaceutical composition comprises any of the following amounts for any one or more of the therapeutic agents:
metformin:about 5.6 g to about 8.4 g;
N-acetyl cysteine: about 8.4 g to about 12.6 g;
poloxamer 188: about 8.4 g to about 12.6 g;
CoQ10: about 1.68 g to about 2.52 g;
cyclosporin A: about 560 mg to about 840 mg;
edaravone: about 168 mg to about 252 mg;
SS-31: about 28 mg to about 42 mg;
sulbutiamine: about 700 mg to about 1050 mg;
vitamin C: about 5.6 g to about 8.4 g; and
zoniporide: about 168 mg to about 252 mg.

In some embodiments, the pharmaceutical composition comprises any of the following amounts for any one or more of the therapeutic agents:
metformin: about 7 g;
N-acetyl cysteine: about 10.5 g;
poloxamer 188: about 10.5 g;
CoQ10: about 2.1 g;
cyclosporin A: about 700 mg;
edaravone: about 210 mg;
SS-31: about 35 mg;
sulbutiamine: about 875 mg;
vitamin C: about 7 g; and
zoniporide: about 210 mg.

The therapeutic agents may be co-administered in any order or even simultaneously. The multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, compositions and formulations are not to be limited to the use of only two agents.

The pharmaceutical composition of the present technology may comprise a pharmaceutically acceptable carrier, such as diluents, disintegrants, sweetening agents, glidants, or flavoring agents and may be formulated into an oral dosage form such as tablets, capsules, powders, granules, suspensions, emulsions, or syrups; or a parenteral dosage form such as liquids for external use, suspensions for external use, emulsions for external use, gels (ointments or the like), inhaling agents, spraying agents, injections, etc. Said dosage forms may be formulated in various forms, e.g., a dosage form for single administration or for multiple administrations.

In some embodiments, the carrier comprises one or more of polyoxyethanyl-α-tocopheryl sebacate (PTS), phosphate buffered saline (PBS), ethanol, polyethylene glycol (PEG), and (bovine serum albumin) BSA.

The pharmaceutical composition of the present technology may include excipients such as lactose, corn starch, or the like, glidants such as magnesium stearate, etc., emulsifying agents, suspending agents, stabilizers, and isotonic agents, etc. If desired, a sweetening agent and/or a flavoring agent may be added. Exemplary excipients include, without limitation, polyethylene glycol (PEG), hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Inorganic salt or buffers include, but are not limited to, citric acid, sodium chloride, potassium chloride, sodium sulfate, potassium nitrate, sodium phosphate monobasic, sodium phosphate dibasic, and combinations thereof.

Suitable antioxidants for use in the present disclosure include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional exemplary excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition disclosed herein may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Non-limiting examples of suitable bases include bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of any individual excipient in the composition will vary depending on the role of the excipient, the dosage requirements of the active agent components, and particular needs of the composition.

Generally, however, the excipient will be present in the composition in an amount of about 1% to about 99% by weight, preferably from about 5% to about 98% by weight, more preferably from about 15 to about 95% by weight of the excipient. In general, the amount of excipient present in a composition of the disclosure is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

The composition of the present technology can be administered orally or parenterally, including inhalation, intravenous, intraperitoneal, subcutaneous, rectal and topical routes of administration. Therefore, the composition of the present technology can be formulated into various forms such as tablets, capsules, aqueous solutions, suspensions, or the like. In the case of tablets for oral administration, carriers such as lactose, corn starch, and lubricating agents, e.g., magnesium stearate, can be conventionally added thereto. In the case of capsules for oral administration, lactose and/or dried corn starch can be used as a diluent. When an aqueous suspension is required for oral administration, the active ingredient can be combined with emulsifying and/or suspending agents. If desired, certain sweetening agents and/or flavoring agents can be added thereto. For intramuscular, intraperitoneal, subcutaneous and intravenous administration, sterile solutions of the active ingredient are usually prepared, and the pH of the solutions should be suitably adjusted and buffered. For intravenous administration, the total concentration of solutes should be controlled in order to render the preparation isotonic. The composition of the present technology may be in the form of an aqueous solution containing pharmaceutically acceptable carriers, e.g., saline having a pH level of 7.4. The solutions may be introduced into a patient's intramuscular blood-stream by local bolus injection.

Methods of Manufacture

In another aspect, a method of preparing a pharmaceutical composition for providing neuroprotection to a brain of a subject suffering from, having suffered from, or at risk of suffering from, cerebral ischemia is provided. Therapeutic agents may be classified as hydrophobic or hydrophilic for the purposes of formulating the compositions of the invention. Those having skill in the art can readily determine hydrophobicity and hydrophilicity of a compound based on properties such as polarity and miscibility with water or organic solvents.

In some embodiments, the method comprises mixing together:
  a) a first mixture comprising one or more hydrophobic therapeutic agents; and
  b) a second mixture comprising one or more hydrophilic therapeutic agents; to form a third mixture.

The first mixture may further comprise one or more hydrophobic carriers described herein and optionally a buffer. The second mixture may further comprise one or more hydrophilic carriers described herein and optionally a buffer and/or an organic solvent.

In some embodiments, the method further comprises mixing the third mixture and a fourth mixture comprising one or more therapeutic agents to form a composition which may be further processed into the final composition.

In another embodiment, the method comprises mixing:
  a) a first mixture comprising CoQ10 and cyclosporin A; and
  b) a second mixture comprising metformin, N-acetyl cysteine, polaxamer-188, edaravone, SS-31, vitamin C, and zoniporide;
to form a third mixture. In some embodiments, the method further comprises mixing with the third mixture a fourth mixture comprising sulbutiamine. In some embodiments, the first mixture further comprises polyoxyethanyl-α-tocopheryl sebacate (PTS) and bovine serum albumin (BSA). In some embodiments, the first mixture further comprises a buffer, for example, PBS.

In some embodiments, the first mixture is formed by mixing:
  i) a mixture comprising CoQ10 and PTS; and
  ii) a mixture comprising cyclosporin A and BSA.

In some embodiments, the mixture of i) and the mixture of ii) each further comprising a buffer, for example, PBS. In some embodiments, the fourth mixture further comprises a $C_1$-$C_6$ alcohol and polyethylene glycol (PEG).

Embodiments described herein are further illustrated by, though in no way limited to, the following working examples.

EXAMPLES

Example 1: Improved Neurological Recovery after Cardiac Arrest in Rats

Summary: Applicant conducted a double blind randomized controlled trial of a pharmaceutical formulation (also referred to as "cocktail") according to the invention in Sprague-Dawley rats (400-500 gm) undergoing 12 min of cardiac arrest. Rats were randomly allocated to receive cocktail or control drugs just after return of spontaneous circulation (ROSC). The drug infusion was done over 20 min using infusion pump. Animals were maintained on ventilator for 2 hrs, during this period, mean arterial pressure (MAP), heart rate (HR), arterial blood gas analysis (ABG) and glucose measurement were done. Rats body temperatures were maintained between 37±0.5° C. throughout the experiment. 2 hrs post ROSC animals were extubated, decannulated, sutured and returned to the animal facility. Outcomes assessed included 72 hrs survival after ROSC and neurological outcome at 24 hrs, 48 hrs and 72 hrs post ROSC.

Materials and Methods: All the experiments were carried out in accordance with the approval of the Institutional Animal Care and Use Committee (IACUC) guidelines. Adult male Sprague-Dawley rats (400-500 gm) were obtained from the Charles River Laboratory (Wilmington, MA) and housed in the animal center on a 12-hour light/dark cycle with free access to water and food. 14 rats were used for control (vehicle injection) and 14 rats were used for cocktail injection (experimental) group with a total of 28 rats. The cocktail was administered to the rats wherein the dosages of each compound (also referred to as drug) in the cocktail are as described in Table 1 below.

TABLE 1

Dosages administered of each compound in cocktail

| S No. | Compound Name | Dose (mg/kg) |
|---|---|---|
| 1 | Metformin | 100 |
| 2 | N-Acetyl Cysteine (NAC) | 150 |
| 3 | poloxamer 188 | 150 |
| 4 | CoQ10 | 30 |
| 5 | cyclosporin A | 10 |
| 6 | edaravone | 3 |
| 7 | SS-31 | 0.5 |
| 8 | sulbutiamine | 12.5 |
| 9 | vitamin C | 100 |
| 10 | zoniporide | 3 |

Cardiac arrest was induced in rats as follows. Rats were anesthetized and put onto a mechanical ventilator under 2% isoflurane. The left femoral artery and left femoral vein was cannulated with polyethylene catheters to measure arterial pressure and drug infusion respectively and wounds were sutured. After surgical preparation and injecting heparin (300 IU) animals were kept for normalizing MAP. The procedure for CA began with injecting vecuronium bromide (2 mg/kg by body weight) slowly administered through the left femoral vein over a 4 min interval. Asphyxial CA was induced by switching off the ventilator and subsequently, discontinuing isoflurane. Mean arterial pressure below 20 mmHg was defined as CA, which was usually observed within ~3 min following the initiation of asphyxia. After 12 min of asphyxia, resuscitation was started with the resumption of ventilation and chest compression under 100% oxygen. 20 sec after the initiation of CPR, a 20 µg/kg bolus injection of epinephrine was administered through the venous catheter. Chest compressions were continued until animals achieve ROSC, which was defined as systolic blood pressure over 60 mm Hg. If ROSC did not occur within 5 minutes of the initiation of CPR, animals were not included in the study.

After inducing 12 min of cardiac arrest (CA) animals were resuscitated by chest compression and once achieved return of spontaneous circulation (ROSC) either control (vehicle) or cocktail were administered intra venous (i.v.) over 20 minutes using infusion pump. Each animal's body temperature was maintained between (36.5-37.5) for 120 min throughout the experiment. The animal's hemodynamics (mean arterial pressure, heart rate, endotracheal $CO_2$) were monitored throughout the experiment. Hemodynamics were recorded after surgical preparation baseline recording of mean arterial pressure, heart rate, $ETCO_2$ were done which continued during CA as well as 2 hrs post ROSC. Hemodynamics parameters were recorded using ADInstruments, USA. Arterial blood gas analysis (ABG) was done to check pH, $pO_2$, $pCO_2$, $HCO_3$, $tCO_2$, lactate and oxygen saturation to maintain and monitor normal physiological condition of the animal. Blood collections were done at baseline, ROSC, 20 min post ROSC, 40 min post ROSC and 2 hrs post ROSC. Blood samples were then centrifuged at 1600 rcf for 10 min to separate the plasma and the collected plasma was used for further biochemical analysis. For arterial blood gas (ABG) analysis pH, $pCO_2$, $pO_2$, $HCO_3$, lactate and oxygen saturation were measured at baseline, 20 min post ROSC and 40 min post ROSC. If the pH, $pCO_2$ and $pO_2$ level were not within the normal range even after 40 min post ROSC then ABG at 60 min post ROSC was measured.

Glucose measurement was done at baseline, at ROSC, 20 min, 40 min and 120 min post ROSC. After 2 hr post ROSC animals were extubated, decannulated and sutured, then after post-operative care provided which included saline infusion and burponex injection subcutaneously then after animals were returned to animal house facility. Every experimental animal was provided daily care which included manually feeding (if unable to eat by itself), significant level of saline and dextrose infusion (if unable to drink) temperature maintenance (by providing heating pad and lamp), and pain relief drug injection. Animals were monitored for long-term (72 hrs) survival. mNDS value was recorded at 24 hrs, 48 hrs and 72 hrs post resuscitation by an experimentally blinded person to observe neurological recovery in controlled and cocktail treated groups as per the Neumar et al., 1995.[15] After 72 hrs of survival and mNDS recording animals were euthanized and whole brain section were taken out for histological analysis of neural degeneration. Blood collection done during experiment was used for biochemical analysis.

Figure 2:
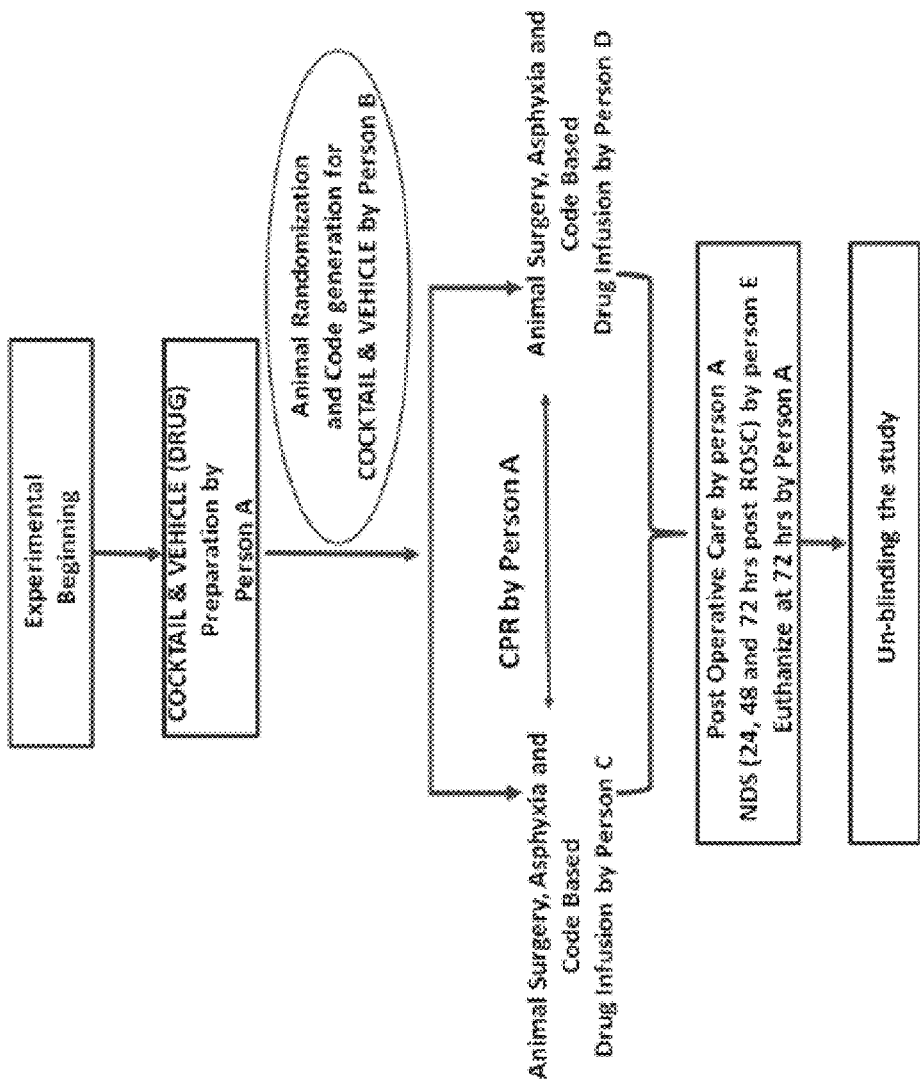
FIG. 2: shows an overall schematic of the experiment of Example 1.

Animal randomization for double blind study: A total of 4 experiments were performed in one day. The animals were randomized for the study and a code was generated for the animal by a person blinded to the experimental conditions. On the day of the experiment, cocktail drug was prepared along with the vehicle separately. The cocktail and vehicle were assigned a code (by the person involved in animal's code generation) and transferred to the surgeon conducting the surgery. Surgeons were blinded to the drug and also to the knowledge of which animal is going to receive cocktail or vehicle. After surgery and induction of 12 min of asphyxia, resuscitation was performed by the person who prepared the cocktail and vehicle. Cocktail or control drug were injected following return of spontaneous circulation (ROSC) depending upon the code generated. Following 2 hrs of ventilation after ROSC animals received post-operative care and were transferred to an animal house. A detailed diagrammatic representation of cocktail double-blind study is shown in FIG. 2, while FIG. 1 details the time-course of the experiment.

Un-blinding the study: Each surgeon tracked the record for the experiment they performed with the drug code injected to the rat. After completion of all the experiments the surgeon was asked to show the list of experiments performed which was matched with the drug code generated to un-blind the study.

Neurological deficit analysis: Recording of Neurological Deficit Scores (NDS) was done at 24 hrs, 48 hrs and 72 hrs post resuscitation. To check the neurological outcome, Applicant modified the NDS recorded as per the behavioral test mentioned by Neumar et al., 1995[15] as tabulated in Table 2 below. In previously mentioned NDS scoring systems, the scoring for respiration was either 0 or 100 thus Applicant changed it to 100 for normal respiration (between 60-120 breath per minute), 50 for breathing between 120-140 and 0 for breathing patterns not falling in those two categories. The NDS values were monitored at 24 hrs, 48 hrs and 72 hrs post resuscitation (NDS, 0-500; 0, brain—dead; 500, normal).

TABLE 2

Modified neurological deficit score (mNDS) values recorder adopted from Neumar et al., 1995

Modified Neurologic deficit scoring system for rats (mNDS)
Parameter Characteristic Score
General 200 points

| Consciousness | Unresponsive 0 | Depressed 50 | Normal 100 |
|---|---|---|---|
| | (<60 >120) | (<120 >140) | Abnormal |
| Respiration | 100 | 50 | 0 |
| Cranial nerves 100 pts | | | |
| Olfactory Orient to smell | no = 0 | yes = 20 | |
| Vision Visual stimulus startle response | no = 0 | yes = 20 | |
| Cornel reflex Blink response to corneal stimulus | no = 0 | yes = 20 | |
| Whisker movement Spontaneous | no = 0 | yes = 20 | |
| Hearing Startle response to loud noise | no = 0 | yes = 20 | |
| Motor 50 pts | | | |
| Left fore paw Spontaneous or withdraw from pain | no = 0 | yes = 10 | |
| Right fore paw Spontaneous or withdraw from pain | no = 0 | yes = 10 | |
| Left hind paw Spontaneous or withdraw from pain | no = 0 | yes = 10 | |
| Right hind paw Spontaneous or withdraw from pain | no = 0 | yes = 10 | |
| Tail Spontaneous or withdraw from pain | no = 0 | yes = 10 | |
| Sensory 50 pts | | | |
| Left forepaw React to pain | no = 0 | yes = 10 | |
| Right forepaw React to pain | no = 0 | yes = 10 | |
| Left hind paw React to pain | no = 0 | yes = 10 | |
| Right hind paw React to pain | no = 0 | yes = 10 | |
| Tail React to pain | no = 0 | yes = 10 | |
| Coordination 100 pts | | | |
| Ledge traverse | no = 0 | yes = 25 | |
| Righting reflex | no = 0 | yes = 25 | |
| Placing test | no = 0 | yes = 25 | |
| Stop at table edge | no = 0 | yes = 25 | |
| Total score | | | |

Biochemical analysis: Collected blood samples at different time interval were used for biochemical assay like-S100B, NSE and 8-hydroxy-2'-deoxyguanosine (8-OHdG). Applicant also measured anti-inflammatory markers to check their changes at different interval.

Histology and staining: After completion of 72 hrs survival animals were perfused through heart with phosphate buffer saline (PBS, 1×, pH=7.4). Whole brain tissue was taken out and transfer to 4% PFA. After further processing with sucrose solution coronal brain section were taken on glass slide, for nissl's staining as well as TUNEL staining. TUNEL staining was done by using ABCAM-TUNEL staining kit.

Statistics: Data for continuous variables are presented as means with a standard error of the mean (SEM). Categorical data are presented as counts with frequencies. An unpaired two-tailed Student's t-test or Mann-Whitney U test was used to compare two independent groups, as appropriate, for continuous variables. One-way or two-way analysis of variance (ANOVA) followed by Sidak's correction for post-hoc comparisons and Kruskal-Wallis test followed by Dunn's multiple comparisons were used for post-hoc comparisons for normally distributed data and non-normally distributed data, respectively. Survival rates were estimated using the Kaplan-Meier method and log-rank test was used to compare the survival curves between groups. Based on the preliminary data, as the mean survival rate at 72 hours after CA was expected as 25% in vehicle-treated rats, 85% in the cocktail-treated rats, we anticipated that 14 rats per group were required in each survival study ($\alpha=0.05$, $\beta=0.2$ [Power=80%], two-sided). Significance was considered at the level of P<0.05. GraphPad Prism 7.0 (GraphPad Software Inc., La Jolla, CA, USA) and SPSS 23.0 (SPSS Inc., Chicago, IL, USA) were used for statistical analyses.

Figure 3:
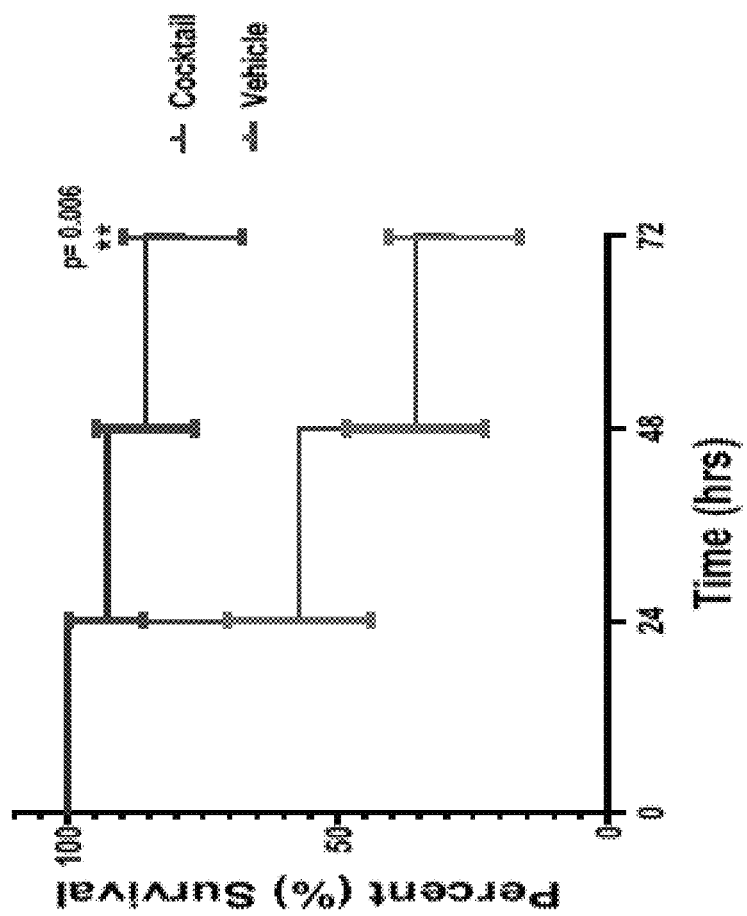
FIG. 3: Kaplan-Meier analyses of 72 hrs survival between cocktail and vehicle injection rat group after 12 min of cardiac arrest and return of spontaneous circulation. Significant difference: **P<0.006 vs the vehicle injection group.

Results: Cocktail drug improved survival rate at 72 hrs after 12 min CA and resuscitation. ROSC was achieved in all 28 rats. All rats that received the experimental drugs were analyzed in this study. There was no significant difference in body weight, hemodynamics or blood gases at baseline between rats treated with vehicle or the cocktail drug (Table 3 & 4). CA occurred at <200 sec after the onset of asphyxia without significant difference between groups and no significant difference in CPR time to ROSC between groups were observed (Table 3). During the first 40 min after ROSC, both the groups did not show a significant difference in pH, partial pressure of carbon dioxide ($pCO_2$), and $HCO_3$. Unexpectedly, arterial oxygen partial pressure ($pO_2$) at 20 min and oxygen saturation ($SaO_2$) of arterial blood samples at 40 min after ROSC was lower in the cocktail group compared to the vehicle group. Arterial lactate and glucose levels at 20 min after ROSC were markedly higher in the cocktail group than in the vehicle group. The survival rate in the vehicle group was 28.6% (5 out of 14) at 72 hrs after CA. The cocktail drug significantly improved survival rates to 78.6% (12 out of 14) (Log Rank P=0.006 vs. vehicle, FIG. 3).

TABLE 3

Variables at baseline and during cardiopulmonary resuscitation

| Baseline Characteristics | Vehicle | Cocktail |
|---|---|---|
| Body Weight (gm) | 450.6 ± 6.9 | 458.1 ± 7.19 |
| MAP (mmHg) | 88.14 ± 3.95 | 89.07 ± 3.63 |
| HR (bpm) | 313.8 ± 13.47 | 295.9 ± 12.08 |
| Esophageal temperature | 36.84 ± 0.11 | 36.93 ± 0.13 |
| Glucose (mg/dL) | 270.5 ± 9.33 | 249.8 ± 19.27 |
| CA characteristics | | |
| Time to Cardiac arrest (sec) | 184.0 ± 6.62 | 193.4 ± 6.61 |
| CPR time to ROSC (sec) | 57.43 ± 2.22 | 57.86 ± 2.21 |

MAP mean arterial blood pressure; HR, heart rate; BPM., beats per minute; CA, cardiac arrest; CPR, cardiopulmonary resuscitation; ROSC, return of spontaneous circulation; sec, second. Values expressed as mean ± SEM

TABLE 4

Arterial blood gas analyses at baseline and at 20 min and 40 min after ROSC

|  | At baseline | At 20 min | At 40 min |
|---|---|---|---|
| PH |  |  |  |
| Vehicle | 7.42 ± 0.01 | 7.23 ± 0.01 | 7.34 ± 0.01 |
| Cocktail | 7.40 ± 0.01 | 7.18 ± 0.02 | 7.31 ± 0.02 |
| pCO$_2$, mmHg |  |  |  |
| Vehicle | 39.91 ± 1.60 | 52.23 ± 2.59 | 41.25 ± 1.64 |
| Cocktail | 43.36 ± 1.16 | 54.84 ± 3.28 | 41.80 ± 2.01 |
| PO$_2$, mmHg |  |  |  |
| Vehicle | 113.4 ± 7.97 | 384.1 ± 35.93 | 128.1 ± 9.33 |
| Cocktail | 109.7 ± 6.79 | 227.9 ± 30.22** | 106.3 ± 17.44 |
| HCO$_3$, mEq/L |  |  |  |
| Vehicle | 25.86 ± 0.85 | 21.99 ± 0.56 | 22.13 ± 0.43 |
| Cocktail | 27.21 ± 0.53 | 20.62 ± 0.63 | 21.20 ± 0.47 |
| SaO$_2$ |  |  |  |
| Vehicle | 98.08 ± 0.42 | 99.33 ± 0.67 | 98.50 ± 0.36 |
| Cocktail | 98.00 ± 0.38 | 97.36 ± 1.42 | 94.86 ± 1.27* |
| Lactate, mmol/L |  |  |  |
| Vehicle | 0.95 ± 0.13 | 3.28 ± 0.25 | 1.80 ± 0.27 |
| Cocktail | 1.11 ± 0.13 | 4.13 ± 0.15** | 2.82 ± 0.39 |
| Glucose, mg/dL |  |  |  |
| Vehicle | 270.5 ± 9.33 | 287.77 ± 18.29 | 194.23 ± 17.81 |
| Cocktail | 249.8 ± 19.27 | 377.5 ± 21.37* | 271.07 ± 28.28 |

Values expressed as mean ± SEM. There were no significant differences at baseline among the groups by mixed-effects model for repeated-measures analyses.
\* = P < 0.05 vs Vehicle,
\*\* = P < 0.005 Vs Vehicle at respective time point.
ROSC return of spontaneous circulation; SaO$_2$, Oxygen saturation.

Figures 4A, 4B, 4C:
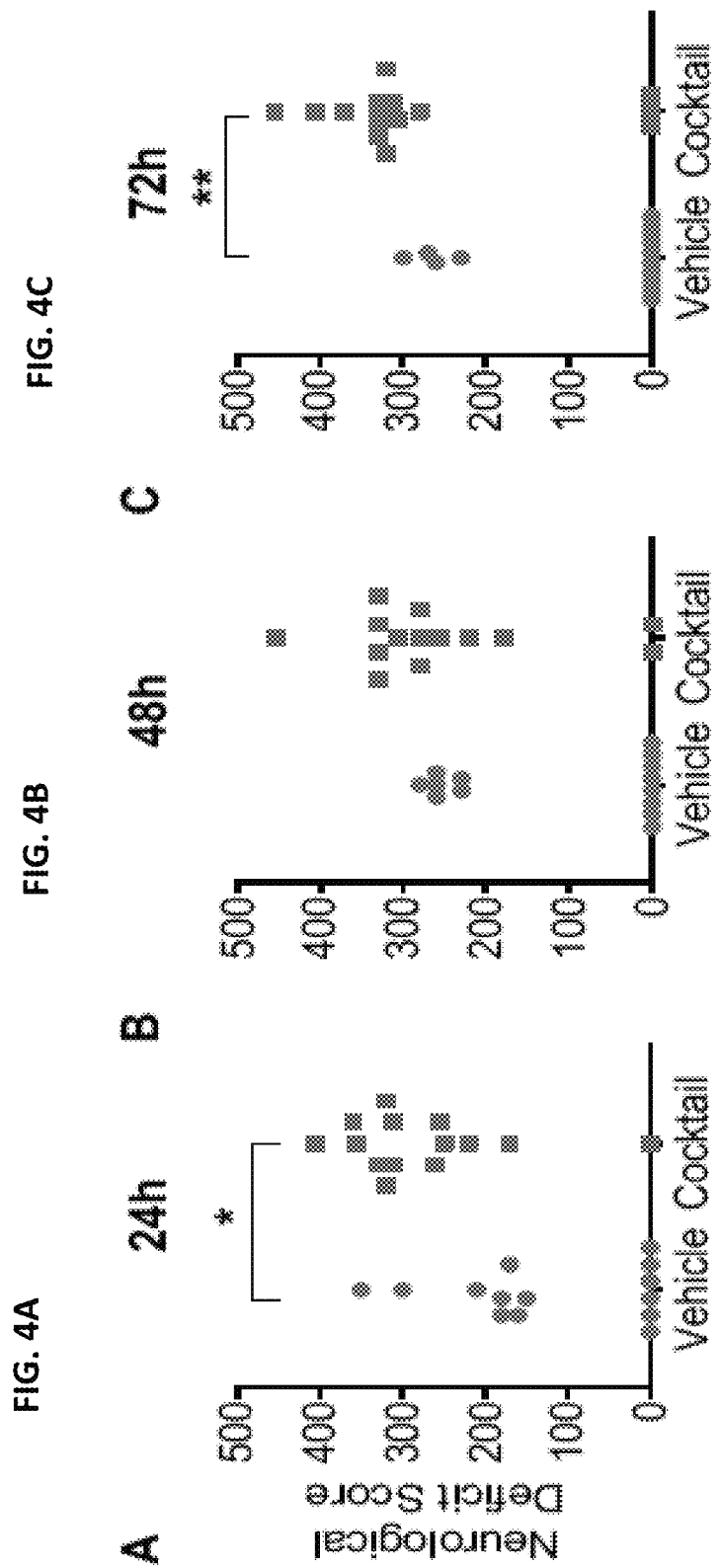
FIG. 4A-4C: Neurological deficit score (NDS) at 24 hrs (FIG. 4A), 48 hrs (FIG. 4B) and 72 hrs (FIG. 4C) between the vehicle and the cocktail injection group after 12 min of cardiac arrest and resuscitation. Dead rats (indicated by score=0) were excluded from the statistical analysis. Statistical significance; *P<0.05, **P<0.005 between groups.

The cocktail prevents neurological dysfunction 72 hrs after CA and resuscitation. Survivors were evaluated for neurological function based on their NDS (0=death or brain death, 500=normal) at 24, 48, and 72 hrs after ROSC. NDS was significantly higher in the surviving rats in the cocktail group (297.3±17.70) than in the vehicle group (212.5±25.76) at 24 hrs after ROSC (P=0.014 by Mann-Whitney test). Although NDS was not significantly different between the groups at 48 hrs after ROSC (P=0.082), the NDS at 72 hrs after ROSC was significantly improved in surviving rats that were treated with the cocktail drugs (341.4±15.12) compared with the vehicle (265.0±14.43) (P=0.004; FIG. 4) treated group. These results suggest that the cocktail drug prevented the development of neurological dysfunction at both early and delayed phases after ROSC in rats.

Figure 5A:
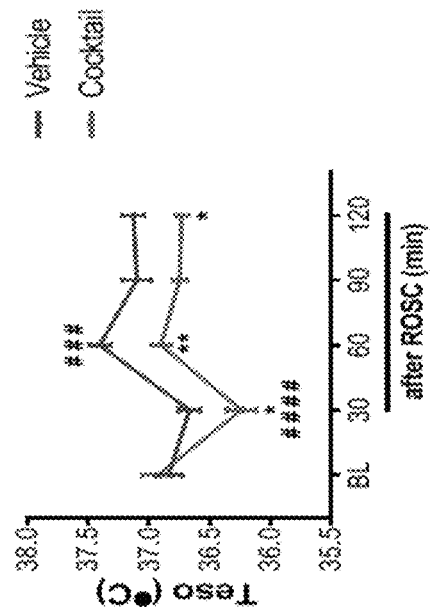
FIG. 5A-5C: shows changes in esophageal temperature, mean arterial pressure, and heart rate during baseline and post-cardiac arrest (CA) care after return of spontaneous circulation (ROSC).
Figure 5C:
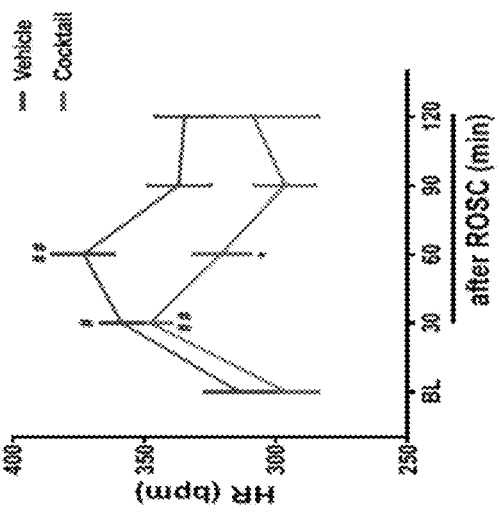
Figure 5B:
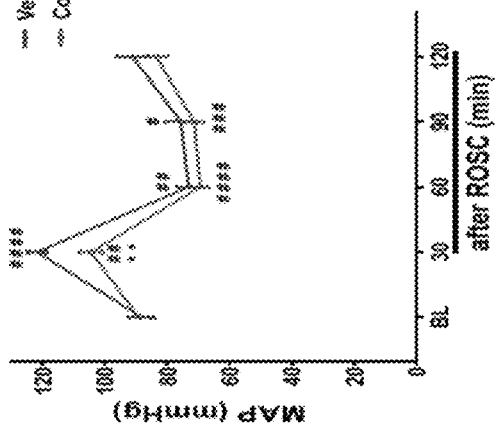

The cocktail drug modified body temperature and hemodynamic parameters early after CA and resuscitation. Although the esophageal temperature was intended to stay between 36.5 and 37.5° C. by an investigator blinded to the identity of the experimental drugs, esophageal temperatures were unintentionally lower in the cocktail group than in the vehicle group at 30, 60, and 120 min after ROSC (FIG. 5A). In both groups, MAP increased at 30 min after ROSC compared with baseline (Vehicle, 121.64±2.94 Vs baseline, 88.41±3.94; p<0.0001; Cocktail 104.38±3.76; Vs baseline, 89.07±3.63; p<0.05;) Thereafter, MAP decreased to of baseline until 90 min after ROSC and subsequently returned to baseline values at 120 min after ROSC. MAP at 30 min after ROSC were markedly lower in the cocktail-treated group (104.38±3.76) compared with vehicle-treated group (121.64±2.94) (p<0.05, FIG. 5B). Thirty minutes after ROSC, HR increased compared with baseline in both groups (Vehicle, 358.54±8.15 Vs baseline, 313.79±13.47; p<0.05; Cocktail 347.74±8.05; Vs baseline, 295.94±12.08) (p<0.005, FIG. 5C). In vehicle-treated group the increased HR was continued until 60 min after ROSC and subsequently returned to baseline values, while heart rate returned to baseline at 60 min and maintained for the remaining period of monitoring in the cocktail-treated group. These observations suggest that the cocktail drug affects the initial hemodynamic changes after resuscitation which are likely associated with the higher survival rate after CA.

The cocktail modified arterial blood gas analysis early after CA and resuscitation. There was a significant decrease in pO$_2$ in cocktail treated group (227.9±30.22) compared with vehicle treated group (384.1±35.93) at 20 min post ROSC; p<0.005 (Table 4) and also a significant decrease in oxygen saturation (SaO2) at 40 min post ROSC between cocktail (94.86±1.27) and vehicle (98.50±0.36) treated group, p<0.05 (Table 4). A significant increase in lactate level was observed at 20 min post ROSC in cocktail injection group (4.13±0.15) compared to vehicle injection group (3.28±0.25) which shows a tendency to returning to the basal level at 40 min post ROSC., p<0.05 (Table 4). Blood glucose level was increased in cocktail treated group (377.5±21.37) at 20 min post-ROSC compared with vehicle group (287.77±18.29), p<0.05 (Table 4) which continued to decrease till further 120 min post ROSC in both groups. These observations suggest that the cocktail drug affects the initial pO$_2$, SaO$_2$ blood lactate and blood glucose changes after resuscitation which are likely associated with the higher survival rate after CA.

Results: The overall goal of the current study was to develop a multi drug cocktail which has a long term survival benefit with good neurological outcomes in a severe CA model by targeting multiple pathways. Applicant observed a very good survival (~78%) in the cocktail injection group compared with the vehicle injection group (~28%) with enhanced neurological outcome in the cocktail treatment group which shows the beneficial effects of the drug cocktail. To rule out the effects of hypothermia, the esophageal temperature (T eso) in both groups was maintained between 37±0.5° C., although a significant difference was observed in T eso between both groups, the observed temperature was within the range (37±0.5° C.), hence the effect of hypothermia is not significant. Furthermore, there was a significant decrease in pO$_2$ in the cocktail injection group compared to the vehicle group at 20 min post ROSC as well as a significant decrease in oxygen saturation (SaO$_2$) at 40 min post ROSC. The observation regarding pO$_2$ suggests that lower oxygen concentration after ROSC is associated with survival and favorable neurological outcomes. Hyperoxia post resuscitation has been shown to increase mortality in patients with mild therapeutic hypothermia.[17-19] The present study suggests that lower oxygen levels at initial stages is beneficial for neuroprotection after CA.

One of the most important findings in this study is the increased lactate and blood glucose levels at the early phase after ROSC in the cocktail treated group (<30 min). The percentage increase in lactate in the cocktail group was higher than in the vehicle injection group at 20 min post ROSC and the lactate clearance percentage in the cocktail injection group after 20 min post ROSC was slower than the vehicle injection group. Since, the cocktail includes a mitochondrial complex I (COX1) inhibitor (e.g. Metformin) and other oxidative phosphorylation (OXPHOS) inhibitors (e.g. N-acetylcysteine), the increased lactate and glucose may be associated with COX1 inhibition[21] which is the major source of ROS generation at early reperfusion (<30 min).

High lactate clearance has been associated with improved outcome in sepsis and post CA, while low lactate clearance is associated with increased mortality.[22] Further, Lee et al., 2013 showed that the lactate clearance rate, and not the initial lactate level was associated with neurological outcomes in OHCA patients after therapeutic hypothermia.[23] The lactate clearance does not predict mortality but is one predictor of improved neurological outcomes.[24] This study suggests that higher lactate and glucose level at initial stages may or may not be associated with survival and favorable neurological outcome.

Example 2: Preparation of Formulation (Cocktail)

Compounds used in the formulation of the invention were first categorized the drug into hydrophilic and hydrophobic chemicals as shown in Table 5.

TABLE 5

Categorization of cocktail drugs into hydrophilic and hydrophobic in nature

| S No | Hydrophilic | S No | Hydrophobic |
|---|---|---|---|
| 1 | Metformin | 8 | CoQ10 |
| 2 | N-Acetyl Cystein | 9 | Cyclosporin A |
| 3 | Poloxamer-188 | 10 | Sulbutiamine |
| 4 | Edaravone | | |
| 5 | SS-31 | | |
| 6 | Vitamin C | | |
| 7 | Zoniporide | | |

All hydrophilic drugs were weighed separately and first dissolved in 750 μL of Poloxamer-188. Separate CoQ10, cyclosporin-A, and sulbutiamine mixtures were made as described below.

CoQ10: 15 mg COQ10 first mixed with 300 μL polyoxyethanyl-α-tocopheryl sebacate (PTS) (already lyophilized at least for 24 hrs) and then incubated in water bath at 60° C. for 15 min). Then 1 ml 1× phosphate buffer saline (PBS) was added, mixed well and again incubated in water bath at 60° C. for 15 min. Sonication was done for 10-15 min.

Cyclosporin A: 5 mg of cyclosporin-A was dissolved in 1.5 ml of 4% BSA prepared in PBS. It was then sonicated for 5 min.

Sulbutiamine: 6.25 mg sulbutiamine first thoroughly mixed with 100 μL Ethanol and then after added 400 μL Polyethylene glycol (PEG). It was then sonicated for 5 min.

After formulation and sonication separately, the CoQ10 (in PTS and PBS) mixture was mixed with the cyclosporin-A (in BSA and PBS) mixture and the resultant mixture was sonicated for 10 min. Then, the hydrophilic drug mixture in polaxamer-188 was mixed with the CoQ10/cyclosporin-A mixture and the resultant mixture sonicated again for 10 min. Finally, the sulbutiamine (with ethanol and PEG) mixture was mixed with the CoQ10/cyclosporin-A/hydrophilic drug mixture and the resultant cocktail mixture was sonicated till a translucent color was observed. The cocktail was then filtered with a 0.45-micron filter and the pH of the solution was adjusted between 7.35-7.45 with sodium bicarbonate.

The control vehicle formulation used in Example 1 was similarly prepared with the exception that it did not include the active compounds of Table 1 and instead of polaxamer-188/PBS was used. Specifically, 300 μL of polyoxyethanyl-α-tocopheryl sebacate (PTS) (already lyophilized at least for 24 hrs) was incubated in water bath at 60° C. for 15 min and then 1 ml 1× phosphate buffer saline (PBS) was added to form a null-CoQ10 mixture (mixture lacking CoQ10). Then after, the null-CoQ10 mixture was agitated and incubated in water bath at 60° C. for 15 min followed by sonication for 5 min. A null-cyclosporin-A (lacking cyclosporin-A) was prepared by mixing BSA with PBS to in proportions to arrive at 1.5 ml of a 4% BSA in PBS mixture. A null-sulbutamine (lacking sulbutamine) mixture was prepared by adding 100 μl of ethanol to 400 μl of PEG. Then the null-CoQ10 mixture, null-cyclosporin-A mixture, and null-sulbutamine mixture were mixed with 750 μl of PBS and sonicated for 2-3 min to produce the vehicle. Vehicle was then filtered with a 0.45-micron filter and the pH was adjusted between 7.35-7.45 with sodium bicarbonate.

REFERENCES

1. Benjamin, E. J., et al. *Circulation* 139, e56-e528
2. Han, F., et al. *Crit Care Med* 36, S447-453
3. Nakka, V. P., et al. *Neurotox Res* 17, 189-202
4. Yin, X. L., et al. *Resuscitation* 83, 378-385
5. Choi, J., et al. *J Am Heart Assoc* 8, e012809
6. Xiang, Y., et al. *Biomed Rep* 5, 11-17
7. Annborn, M., et al. *Resuscitation* 84, 782-787
8. Dell'anna, A. M., et al. *Resuscitation* 85, 932-938
9. Adrie, C., et al. *Circulation* 106, 562-568
10. Matsumoto, T., et al. *Lab Invest* 77, 119-125
11. Morganti-Kossman, M. C., et al. *Mol Psychiatry* 2, 133-136
12. Zhu, J., et al (2018) *J Am Heart Assoc* 7
13. Zhang, J., et al. (2020) *Oxid Med Cell Longev* 2020, 7468738
14. Sharp, W. W., et al. *Crit Care Med* 43, e38-47
15. Neumar R W, et al. *Resuscitation* 29, 249-263
16. Han, F., et al. *Resuscitation* 81, 93-99
17. Janz, D. R., et al. *Crit Care Med* 40, 3135-3139
18. Kilgannon, J. H., et al *JAMA* 303, 2165-2171
19. Elmer, J., et al. *Intensive Care Med* 41, 49-57
20. Storm, C., et al. *Scand J Trauma Resusc Emerg Med* 24, 43
21. Piel, S., et al. *Acta Physiol (Oxf)* 213, 171-180
22. Nguyen, H. B., et al. *Crit Care Med* 32, 1637-1642
23. Lee, T. R., et al. *Crit Care* 17, R260
24. Donnino, M. W., et al. *Resuscitation* 75, 229-234
25. Zheng Z J, et al *Circulation.* 104 (18): 2158-63. doi: 10.1161/hc4301.098254. PMID 11684624.
26. Kronick S L, et al *Circulation.* 132 (18 Suppl 2): S397-413. doi:10.1161/cir.0000000000000258. PMID 26472992.
27. Cydulka, Rita K., editor. (2017-08-28). *Tintinalli's emergency medicine manual*. ISBN 9780071837026. OCLC 957505642.
28. *Continuing Education in Anaesthesia Critical Care & Pain*, Volume 12, Issue 6, December 2012, Pages 283-287

Example 3: Multidrug Cocktail Therapy Improves Survival and Neurological Function after Cardiac Arrest in Rodents Cardiac arrest (CA) is a leading cause of death in the United States. Yet little progress has been made in developing therapies that substantially improve survival and neurological outcomes. CA causes global ischemia and neuronal degeneration via multiple pathways, such as oxidative, inflammatory, and metabolic stress. Current treatments for neuroprotection after CA mainly target a few damage-causing pathways without addressing the multitude of other injuries. In this study, we sought to develop a multidrug cocktail therapy that can simultaneously target multiple affected pathways implicated in ischemia-reperfusion injury. We also evaluated the effectiveness of the cocktail in improving neurologically intact survival after cardiopulmonary resuscitation in a severe injury rat model CA.

Methods: We developed a multidrug cocktail comprising 10 drugs that target distinct aspects of ischemia-reperfusion injury, with an emphasis on survival and neuroprotection. We conducted a prospective, randomized, blinded, placebo-controlled study in male Sprague-Dawley rats undergoing 12 min of asphyxial-CA. Rats were resuscitated and immediately following return of spontaneous circulation (ROSC), they were randomly assigned to receive either the cocktail (n=14) or vehicle (n=14) intravenously. Rats were maintained on mechanical ventilation for 2 h to monitor hemodynamics and analyze arterial blood gas and glucose. Outcomes assessed include 72 h survival and neurological function at 24, 48, and 72 h post-ROSC. Brains were also evaluated with histological staining to analyze morphological changes in cells after the cocktail was administered.

Results: We found that the cocktail significantly improved 72 h survival: 78.6% of cocktail-treated rats survived versus 28.6% of vehicle-treated rats (log-rank test; P=0.006). Two neurological deficit scores indicated substantially improved neurological function at 72 h in cocktail-treated rats versus vehicle-treated rats (P=0.004 for Scale 1 and P=0.013 for Scale 2).

Conclusions: In a randomized controlled study using a lethal rodent model of 12 min asphyxial-CA, our multidrug cocktail significantly improved 72 h survival and neurological outcomes suggesting that a multidrug cocktail may be effective at timepoints when our current therapies fail.

Abbreviations

ANOVA one-way analysis of variance
ATP adenosine triphosphate
ATP-MgCl2 adenosine triphosphate-magnesium chloride
BBB blood-brain barrier
BPM breaths per minute
bpm beats per minute
CA cardiac arrest
CPR cardiopulmonary resuscitation
ESI-MS electrospray ionization mass spectrometry
ETCO2 end-tidal CO2
HR heart rate
MAP mean arterial pressure
mNDS modified neurological deficit score
mPTP mitochondrial permeability transition pore
NDS neurodeficit score
NHE-1 sodium-hydrogen exchanger isoform-1
PBS phosphate buffer saline
PFA paraformaldehyde
pO2 partial pressure of oxygen
PTS polyoxyethanyl-α-tocopheryl sebacate
ROS reactive oxygen species
ROSC return of spontaneous circulation
SaO2 oxygen saturation
SEM standard error of the mean
SS-31 Szeto-Schiller peptide-31
TUNEL terminal deoxynucleotidyl transferase dUTP nick end labeling

Clinical Perspective

We developed a multidrug cocktail therapy comprising 10 neuroprotective drugs. We assessed the effectiveness of the multidrug cocktail in a rodent model of 12 min cardiac arrest followed by cardiopulmonary resuscitation in a blinded, randomized, placebo-control study. Our multidrug cocktail therapy was associated with improved neurological function and survival after cardiac arrest.

The global ischemia-reperfusion injury following cardiac arrest produces severe multiorgan damage, especially in the brain, that requires novel multifaceted therapies for protection after cardiac arrest. Treating with a multidrug cocktail after cardiac arrest successfully improved survival with favorable neurological outcomes that could be translated to human patients.

Introduction

Cardiac arrest (CA) accounts for more than 360 000 deaths in the United States, with a mortality rate of nearly 90%.[1] Despite such high mortality, little progress has been made in developing pharmacological interventions that substantially improve survival and neurological outcomes.

CA is a complex condition that suddenly reduces blood flow to all organs in the body, resulting in global ischemia.[2] During resuscitation, oxygen is reintroduced, producing reperfusion injury that augments the previous ischemic damage. After CA, brain injury and poor survival occur due to a complex cascade of events, including mitochondrial dysfunction[3], endoplasmic reticulum stress[4]; depletion of high-energy metabolites, such as adenosine triphosphate (ATP)[5]; oxidative injury[6]; and an inflammatory response[7]. These events lead to cell death and impair neurological functions. CA also affects other organs. For example, organ metabolomic profiling after prolonged CA showed resuscitation-mediated metabolite dysfunction.[8] Furthermore, metabolic dysregulation post-resuscitation was similarly observed in rodents and humans[9], indicating whole-body injury, amelioration of which requires a multidimensional approach, such as a combination therapy.

As a global disease, there are a multitude of metabolic, energetic, and inflammatory pathway alterations. Although several studies aimed to discover neuroprotective drugs that offer benefits after ischemic injury", most use only a single drug. This approach is valuable for understanding more about CA pathology and to design improved therapies. However, due to the severity and complexity of CA injury single-drug therapies are not enough to confer protection in humans. The effects of CA on multiple organs require a more complex approach for treatment. A few studies have combined drugs as an individual pharmacologic intervention or in combination with therapeutic hypothermia.[11,13] These studies have two major limitations: they use a minimum number of therapeutic agents that cannot target the majority of injury pathways, and they have not been tested in more severe CA models, which require a more inclusive approach for treatment. Multidrug cocktails have also been used to treat other diseases, such as HIV/AIDS,[14] cancer,[15] and coronavirus disease 2019.[16] This broad applicability shows the real-world strength of using multidrug cocktails to treat complex diseases, such as ischemia-reperfusion injury. However, this multidrug approach has not been explored in CA.

In this blinded randomized, placebo-control study, our objective was to develop a multidrug cocktail and determine the efficacy of the cocktail in improving 72 h survival and neurologic outcomes in a rodent model of asphyxial-CA and resuscitation.

Methods

Selection and Formulation of the Multidrug Cocktail

We aimed to develop a multidrug cocktail containing a complex mixture of agents with different physical and chemical properties. Our goal was to provide the most benefit with the least number of agents in a single concoction. To produce an effective cocktail, included drugs must be evaluated for their ability to confer either survival and/or neuroprotection following CA in clinical or preclinical settings. This information can aid in selecting agents that can be appropriately and practically combined. We thoroughly searched the literature and selected 10 neuroprotective drugs to include in our multidrug cocktail: metformin, N-acetyl cysteine, poloxamer 188, edaravone, Szeto-Schiller peptide-31 (SS-31), vitamin C, zoniporide, CoQ10, cyclosporin A, and sulbutiamine (published dosages and pathways are listed in Table 6). Each drug, individually and in various combinations, was administered to normal rats (n=3) to determine any potential adverse effects, such as immediate death. We conducted sequential iterations of cocktail development and preliminary trials (see Table 9 in the Data Supplement) and arrived at a final formulation (see Table 10 and the Methods in the Data Supplement).

The vehicle used in our study contained all elements of the multidrug cocktail except for the 10 drugs.

TABLE 6

Ten Pharmaceutical Agents in the Cocktail Therapy

| Agent | Dose, mg/kg | Mechanism(s) of action | Reference |
| --- | --- | --- | --- |
| Metformin | 100 | Reversibly inhibits mitochondrial complex I, reduces ROS and inflammation, protects the BBB, promotes neurogenesis | 34 |
| N-acetyl cysteine | 150 | Antioxidant, anti-inflammatory | 35 |
| Poloxamer 188 | 150 | Lipid bilayer stabilizer; reduces BBB damage, brain edema and cellular death | 36 |
| CoQ10 | 30 | Antioxidant; increases resistance to oxidative stress, improves mitochondrial bioenergetics | 37 |
| Cyclosporin-A | 10 | Inhibits mPTP, reduces release of cytochrome c, increases superoxide dismutase activity | 12 |
| Edaravone | 3 | Antioxidant, ROS scavenger, reduces free radical-induced inflammation, prevents lipid peroxidation, reduces cellular oxidative damage | 38 |
| SS-31 | 0.5 | Protects mitochondrial membrane, stabilizes cardiolipin | 39 |
| Sulbutiamine | 12.5 | Metabolic supplement for brain energetics, easily crosses the BBB, increases thiamine level | 40 |
| Vitamin C | 100 | Antioxidant, protects against oxidative stress, cofactor in catecholamine synthesis | 41 |
| Zoniporide | 3 | Inhibits NHE-1, protects ionic gradients, decreases calcium overload from ischemia | 42 |

Abbreviations: BBB indicates blood-brain barrier; mPTP indicates mitochondrial permeability transition pore; NHE-1 indicates sodium-hydrogen exchanger isoform-1; ROS indicates reactive oxygen species.

Detailed Protocol for Formulating the Multidrug Cocktail and Vehicle

All hydrophilic drugs were weighed separately and dissolved in 750 poloxamer 188. Hydrophobic drugs were first formulated separately and then combined to form the full cocktail. CoQ10 (15 mg) was initially dissolved in 300 µL polyoxyethanyl-α-tocopheryl sebacate (PTS; 15% w/v in water) that was previously lyophilized for 24 hours. This combined mixture was incubated in a 60° C. water bath for 15 min. Then phosphate buffer saline (PBS 1×; 1 mL) was added to the mixture, which was then vortexed, incubated in a 60° C. water bath for 15 min, and sonicated for 10 to 15 min. Cyclosporine A (5 mg) was dissolved in 1.5 mL 4% BSA prepared in 1×PBS and sonicated for 5 minutes. Sulbutiamine (6.25 mg) was thoroughly dissolved in 100 µL absolute ethanol. Then 400 µL polyethylene glycol 300 (PEG-300) was added to the mixture, which was then sonicated for 5 min. After completing the individual formulations for each hydrophobic drug, the formulations for CoQ10 and cyclosporine A were combined and sonicated for 10 min. This mixture was combined with the solution of all hydrophilic drugs and sonicated again for 10 min. Finally, the sulbutiamine formulation was added to the mixture, and the whole solution was sonicated until the solution was translucent. The cocktail was filtered through a 0.45 µm syringe filter, and the pH was adjusted to between 7.35 and 7.45 using sodium bicarbonate (50 mEq) (0.8-1.0 mL). The final volume of the cocktail was approximately 4.5 mL.

Vehicle was formulated similar to the cocktail. Instead of poloxamer 188, PBS (1×; 750 µL) was used as the solubilizing agent. PTS (300 that was previously lyophilized for 24 h was incubated in a 60° C. water bath for 15 min to which 1 mL 1×PBS was added. The solution was incubated in a 60° C. water bath for 15 min and then sonicated for 5 min. This mixture was combined with 1.5 mL 4% BSA prepared in 1×PBS, and 100 µL absolute ethanol was added to 400 µL PEG. Then all solutions were combined and sonicated for 2 to 3 min. Vehicle was also filtered through a 0.45-µm syringe filter, and the pH was adjusted to 7.35 to 7.45 using sodium bicarbonate.

Evaluation of Active Cocktail Components Using Mass Spectrometry

Figure 6:
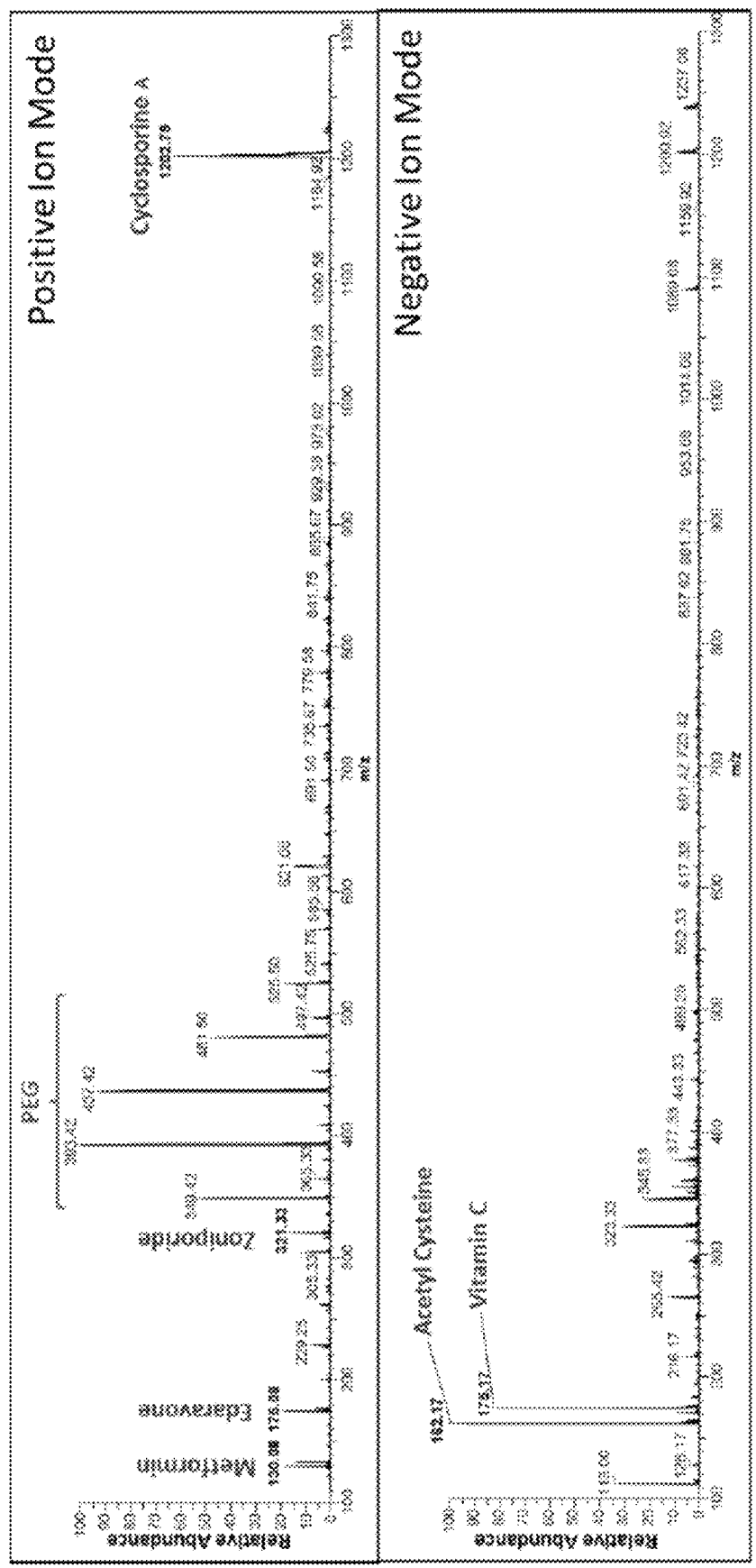
FIG. 6: Electrospray ionization/mass spectrometry (ESI/MS) analysis of the 10-drug cocktail. Positive ion mode (top) and negative ion mode (bottom) after ethyl acetate extraction of the cocktail. Analysis shows the m/z (mass/charge) values for the major ingredients (metformin, edaravone, zoniporide, cyclosporine A, N-acetyl cysteine, and vitamin C, and traces of polyethylene glycol (PEG)). The remaining drugs were not detected and require a more complex extraction and analysis methodology.

After developing the final formulation of our cocktail, we confirmed the stability and/or molecular interaction of the drugs in our formulation with mass spectrometry (MS). To separate the individual drugs from the cocktail formulation, we applied a liquid/liquid extraction methodology" using ethyl acetate. Then the molecular mass of the extracted components was analyzed by electrospray ionization mass spectrometry (ESI-MS) (FIG. 6). For the extraction, 500 µL of the cocktail formulation was mixed with 1000 μL ethyl acetate and then vortexed for 30 seconds. Then the preparation was centrifuged at 10 000 g for 2 min at room temperature. The top layer (ethyl acetate) was then separated and transferred to a new vial. Another 1000 ethyl acetate was added into the bottom layer, and the extraction was repeated. The combined organic phase was dried with nitrogen gas. The residue was reconstituted in 500 μL methanol, vortexed for 10 s, and centrifuged at 13 000 g for 2 min. The final extract was transferred into a polypropylene vial. Then 30 μL of the final extract was injected and analyzed on a LTQ XL™ Linear Ion Trap Mass Spectrometer (Thermo Fisher Scientific, Waltham, MA), and the data was analyzed using Xcalibur 3.1 (Thermo Fisher Scientific, Waltham, MA).

Animal Experimental Procedure for 12 Min of Asphyxial-Cardiac Arrest

Figure 7:
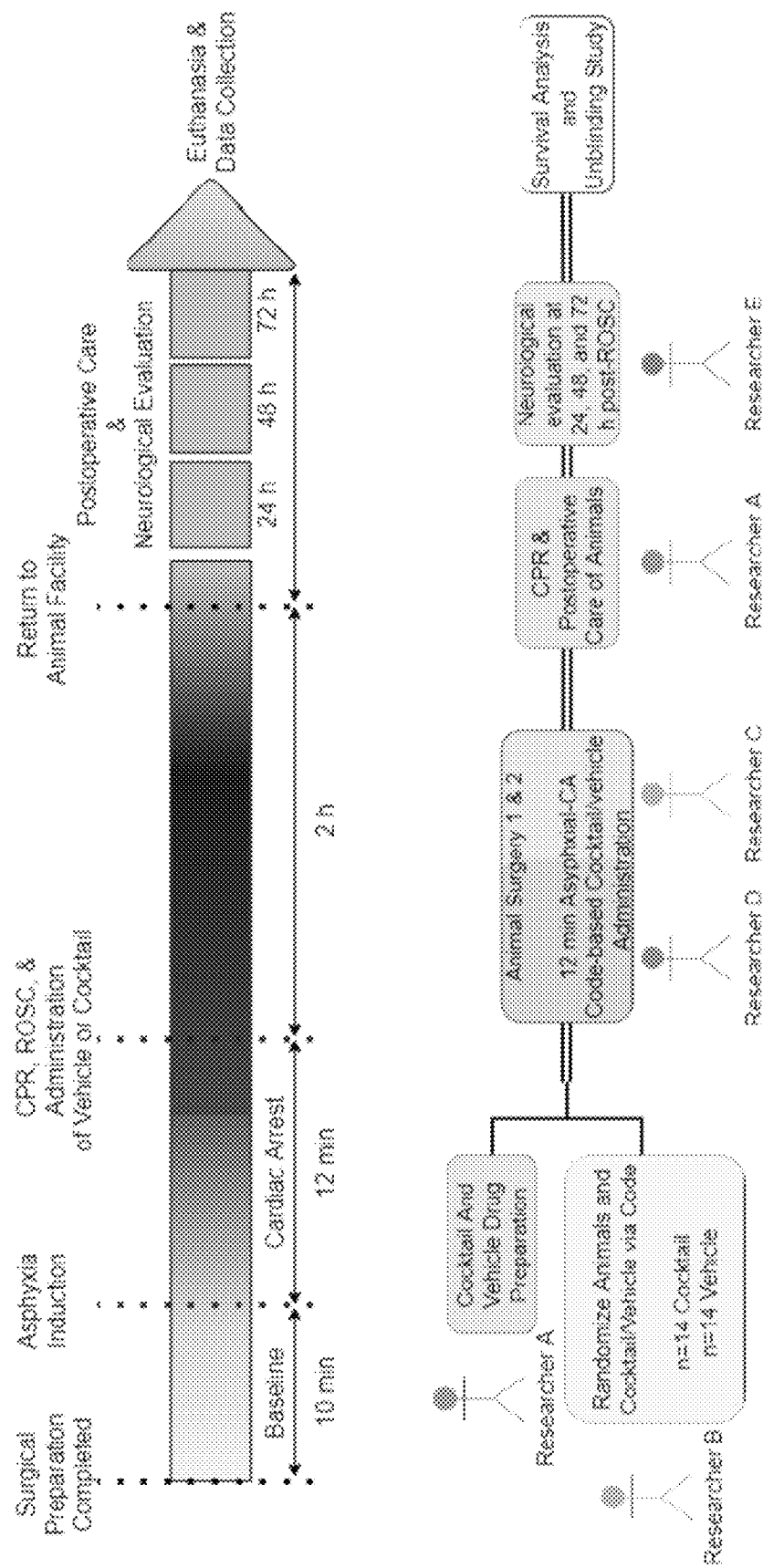
FIG. 7: Schematic diagram of procedure and timeline for blinded experiments. Top indicates the timeline of the rat CA experiment up to 72 h survival; bottom indicates the methodology for conducting the survival study in a blinded manner. CPR, cardiopulmonary resuscitation; ROSC, return of spontaneous circulation.

All experiments were carried out in accordance with the approval of the Institutional Animal Care and Use Committee (IACUC) guidelines. The procedures for inducing asphyxia in male Sprague-Dawley rats (Charles River Laboratory, Wilmington, MA) weighing 400 to 500 g, was as previously published[18] (see Methods in the Data Supplement). The exploration of effect modification caused by the gender difference is far beyond the current aspect of our study and so we used only male animals in this study to reduce the potential outcome variability that might be affected by the gender difference. Briefly, rats were assigned to 2 groups: cocktail-treated and vehicle-treated. After surgical preparation and 12 min of asphyxial-CA, resuscitation was started by resuming mechanical ventilation at 100% oxygen and beginning chest compressions.[18] Rats received either cocktail or vehicle immediately after ROSC, and mechanical ventilation continued for 2 h post-ROSC. Rats were then returned to the animal housing facility and provided daily care according to the approved protocol. Rats were monitored for survival up to 72 h post-ROSC, and neurological evaluation was performed at 24, 48, and 72 h post-ROSC by a blinded researcher using 2 scoring scales.[19, 20] At 72 h, rats were euthanized, and whole brain was harvested for histological analysis of neuronal degeneration (FIG. 7).

Blinded, Randomized, Placebo-Control Study

Rat experiments were performed in a randomized and blinded manner. Cocktail and vehicle were freshly prepared in excess and in a non-identifiable manner by Researcher A. Researcher B randomly assigned the cocktail or vehicle and was blinded to all experimental conditions. Two surgeons, Researchers C and D, performed the animal surgeries and administered the treatments after successful ROSC in a blinded manner. After 12 min of asphyxial-CA, cardiopulmonary resuscitation (CPR) via chest compressions was performed by Researcher A to maintain consistency during the resuscitation process. At 2 h post-ROSC, animals received post-operative care and were transferred to the animal housing facility. Neurological evaluation was performed by Researcher E.

Neurological Deficit Scores at 24, 48, and 72 h Post-Resuscitation

To evaluate neurological outcomes, we used 2 scales (Scale 1[19] and Scale 2[20]). The neurological deficit scale (NDS) attempts to capture the overall functionality of the rats that includes overall general appearance, such as consciousness, cranial nerve functionality, motor and sensory capabilities, and overall coordination skills. We modified the binary respiration score in Scale 1 from 0 or 100 to include 50:100 indicated normal respiration between 60 and 120 breaths per minute (BPM), 50 indicated respiration between 120 and 140 BPM, and 0 indicated breathing patterns outside of those ranges (see Table 10 in the Data Supplement). Neurological function was evaluated 24, 48, and 72 h post-ROSC (mNDS ranging from 0-500 with 0 indicating dead and 500 indicating normal animal). A secondary neurological evaluation (Scale 2) was used with a scale ranging from 0 to 80, such that 0 represents brain-dead and 80 represents normal (see Table 11 in the Data Supplement).

Histology and Staining

At 72 h post-ROSC, surviving rats were placed under anesthesia and transcardially perfused with cold phosphate buffer saline (PBS; 1×, pH=7.4). Whole brains were harvested and fixed in 4% paraformaldehyde (PFA) at 4° C. Following cryopreservation in 30% sucrose solution in PBS, serial coronal sections (14 μm) were cut on a cryostat (CM1900, Leica) and collected on glass slides. Nissl (Cresyl Violet, Acros Organics, USA) and TUNEL (terminal deoxynucleotidyl transferase dUTP nick end labeling) (Abcam, UK) staining were performed according to the manufacturer's instructions and as previously published.[20] Hippocampal CA1/CA3 pyramidal neurons were imaged using a BX-X800 bright field microscope (Keyence, USA). The BX-X800 Analyzer (Keyence, USA) was used to semi-quantify ischemic cells (Nissl staining) and apoptotic cells (TUNEL staining). Sham rats were anesthetized deeply prior to the same perfusion and fixation method for brain histology as experimental rats. To compare brain histology between the surviving rats (sham, vehicle-treated, and cocktail-treated; n=4 each), we used one-way analysis of variance (ANOVA) followed by Tukey's correction for post-hoc comparison.

Statistical Analyses

Data for continuous variables are presented as mean±standard error of the mean (SEM). Categorical data are presented as frequencies with proportions. For hemodynamic parameter measurements (vehicle-treated and cocktail-treated; n=14 each), differences were compared with repeated measures two-way ANOVA followed by Tukey's correction for post-hoc comparison within the same group and by Sidak's correction for post-hoc comparison between groups. We compared lactate and glucose measurements for all rats using repeated measured mixed-effects analysis followed by Tukey's correction for post-hoc comparison within the same group or Sidak's correction for post-hoc comparison between groups. Mixed-effects analysis was used because the instrument malfunctioned at a few time points, resulted in missing values. For other analyses, either an unpaired two-tailed Student's t test or Mann-Whitney U test was used to compare 2 independent groups for continuous variables, as appropriate. The proportion of rats surviving up to 72 h was evaluated using the log-rank test to compare the survival curves between the 2 groups. Our preliminary analysis of survival (see FIG. 11 in the Data Supplement) showed the mean survival rate at 72 h after CA was 25% in vehicle-treated rats and 85% in cocktail-treated rats. Therefore, we anticipated that 14 rats per group for each survival study would be appropriate to detect a 60% difference in survival between the 2 groups (α=0.05, β=0.2 [Power=80%], two-sided). Statistical significance was set at P<0.05. GraphPad Prism version 8.4 (GraphPad Software Inc., La Jolla, CA, USA) and SPSS version 23.0 (SPSS Inc., Chicago, IL, USA) were used for statistical analyses.

Results

Preliminary Analysis of the Multidrug Cocktail

The cocktail formulation required multiple iterations during development. We conducted 8 preliminary trials with various formulations and combinations before generating the final cocktail (see Table 9 in the Data Supplement). Each trial provided information regarding the functionality of the cocktail and potential adverse effects in control and CA rats. With each preliminary trial, we learned areas for modification, such as (1) the rate of infusion should minimize hemodynamic fluctuations, (2) the pH should be adjusted with sodium bicarbonate, and (3) ATP-magnesium chloride should be removed due to its hypotensive effect. After several attempts, we formulated the final drug cocktail.

FIG. 6 shows the mass spectra of the cocktail drugs, indicating that metformin, edaravone, zoniporide, cyclosporine A, N-acetyl cysteine, and vitamin C are intact and stable.

Figures 12A, 12B, 12C:
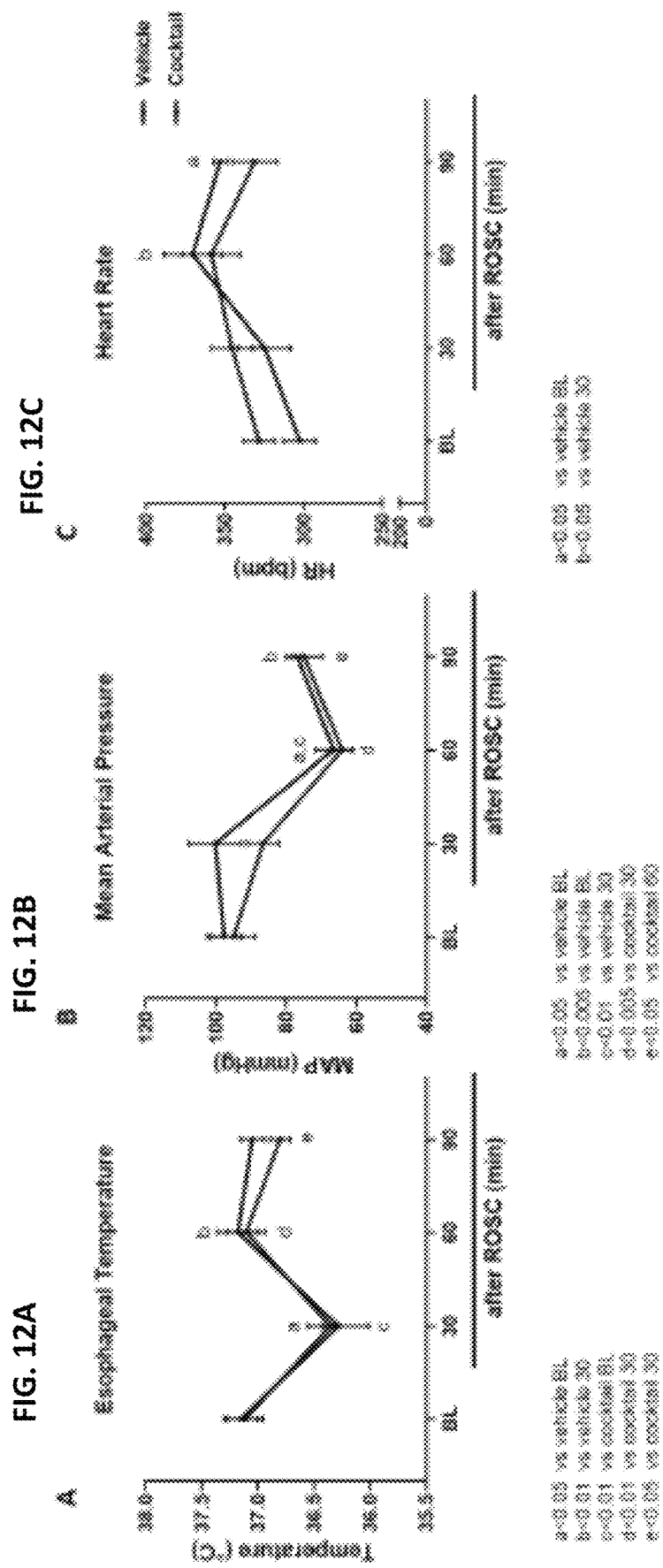
FIG. 12A-12C. Preliminary study of esophageal temperature and hemodynamic changes in cocktail-treated and vehicle-treated rats after cardiac arrest. A through C, Changes in (FIG. 12A) esophageal temperature, (FIG. 12B) mean arterial pressure (MAP), and (FIG. 12C) heart rate (HR) at baseline (BL) and after return of spontaneous circulation (ROSC) in the preliminary study. No major differences occurred between vehicle-treated and cocktail-treated rats. Data are presented as mean±SEM, and significance comparisons intragroup are shown in the inserts. Bpm stands for beats per minute.
Figure 13B:
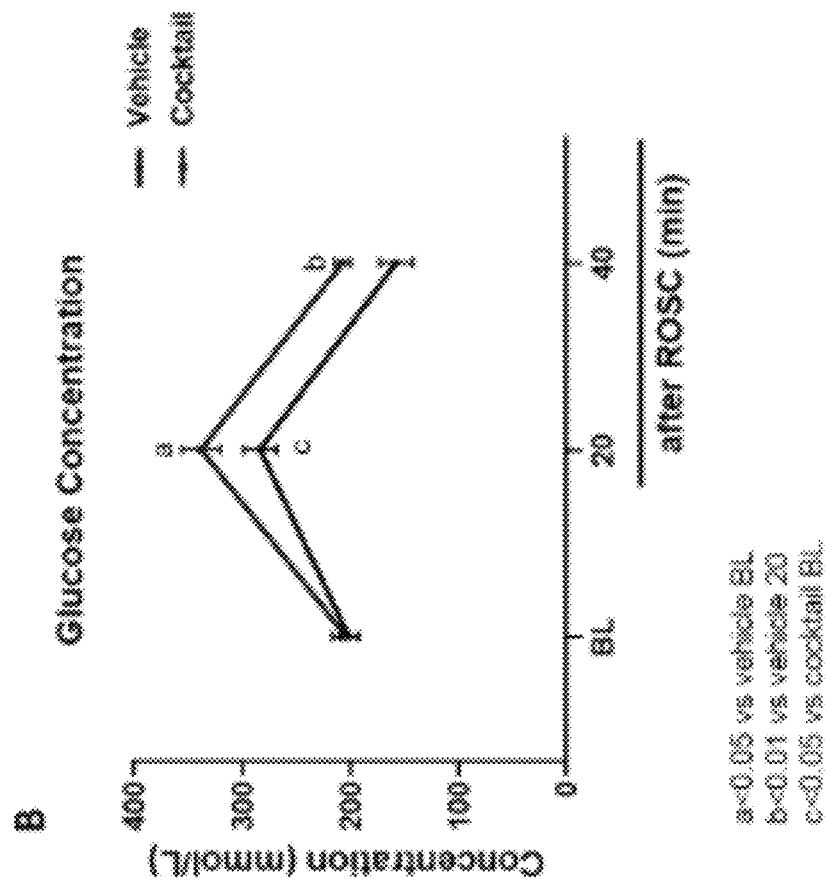
FIG. 13A-13B. Preliminary study of lactate and glucose concentration in cocktail-treated and vehicle-treated rats after cardiac arrest. A and B, Changes (FIG. 13A) blood lactate and (FIG. 13B) glucose concentrations at baseline (BL) and after return of spontaneous circulation (ROSC). No major differences occurred between vehicle-treated and cocktail-treated rats. Data are presented as mean±SEM, and significance comparisons intragroup are shown in the inserts.
Figure 13A:
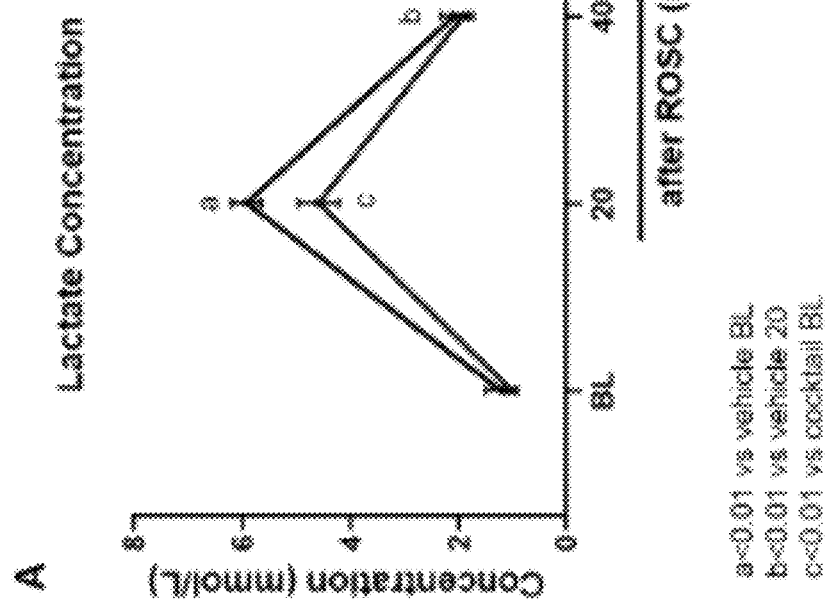

Our results laid the foundation for a blinded experiment to assess the effectiveness of the cocktail. First, an unblinded, preliminary study determined the survival and neuroprotective difference between vehicle-treated (n=5) and cocktail-treated (n=6) rats (for a total of 11 rats). Rats underwent 12 min asphyxial-CA, and immediately after achieving ROSC, they were injected with either vehicle or cocktail. Then, we assessed differences in the survival, neurological function, hemodynamics, glucose, and lactate in these rats (FIGS. 11-13). These preliminary experiments demonstrated improved survival and neurological function.

Cocktail Improves Survival and Mitigates Neurological Dysfunction and Brain Damage after Asphyxial-Cardiac Arrest At 72 h after asphyxia-CA, the survival rate was 28.6% (5/14) in vehicle-treated rats and 78.6% (12/14) in cocktail-treated rats, indicating that the cocktail therapy significantly improved the rate of survival (P=0.006) (FIG. 8A). Surviving animals were evaluated for neurological function at 24, 48, and 72 h after ROSC with 2 neurological scales (Scale 1 and Scale 2; see Table II and III in the Data Supplement). At 24 hours after ROSC, the score from Scale 1 was significantly higher in surviving rats treated with cocktail (297.3±17.7) versus those treated with vehicle (212.5±25.8) (P=0.014) (FIG. 8B). At 48 h post-ROSC, we noticed an improving, but not statistically significant, trend between the groups, with the cocktail group showing a potentially greater retention of neurological function (P=0.082) (FIG. 8B). At 72 h post-ROSC, neurological function was significantly higher in surviving rats treated with cocktail (341.4±15.1) versus those treated with vehicle (265.0±14.4) (P=0.004) (FIG. 3B). With Scale 2, neurological function was also significantly improved in cocktail-treated rats versus vehicle-treated rats at 24 (P=0.190), 48 (P=0.037), and 72 (P=0.013) h post-ROSC (FIG. 8C). These results support that the cocktail therapy mitigated neurological dysfunction in rats in a severe model of CA injury.

Figures 9A, 9B:
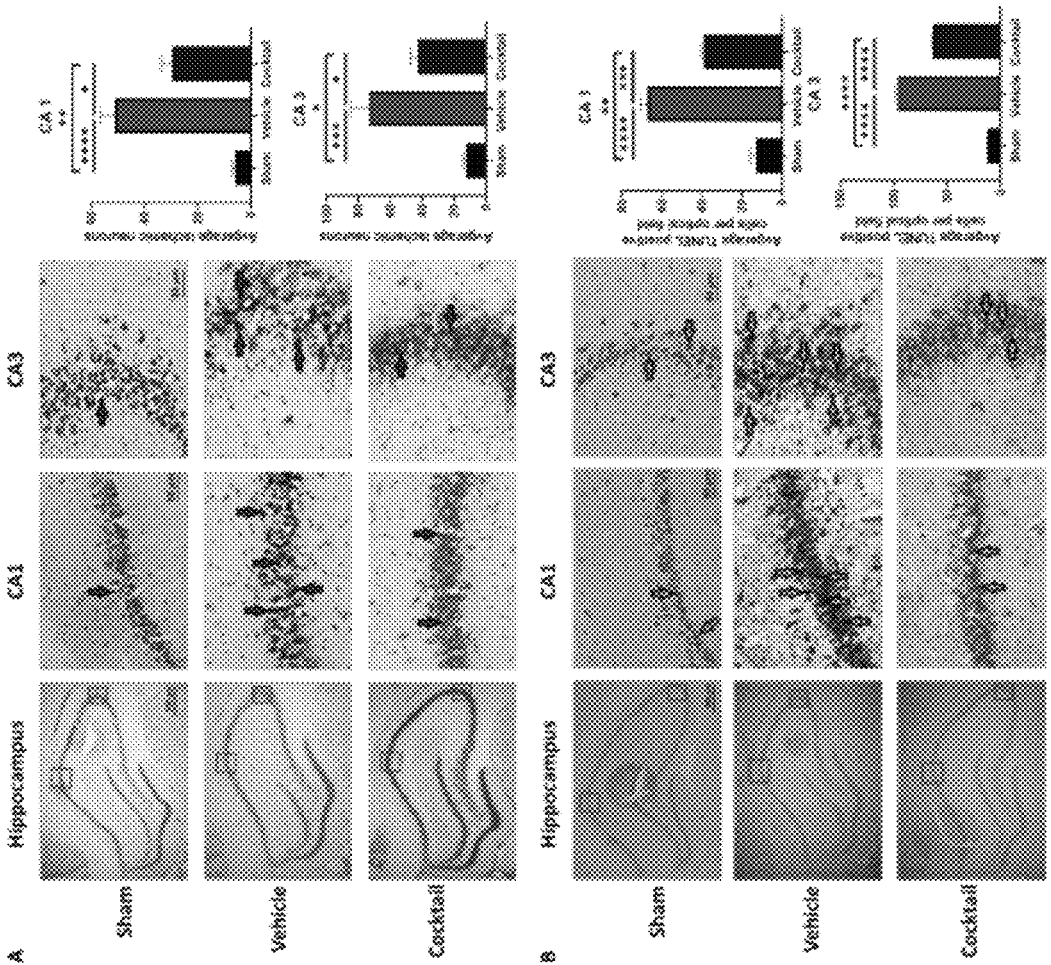
FIG. 9A-9B. Cocktail improves brain histology after asphyxial cardiac arrest and resuscitation.

We assessed brain morphology in vehicle-treated and cocktail-treated rats by histological analyses with Nissl and TUNEL staining. In the hippocampal CA1 and CA3 fields of the left cerebral hemisphere, we detected ischemic cells with Nissl staining and apoptotic cells with TUNEL staining. In both regions of the hippocampus, the average number of ischemic neurons was significantly higher in vehicle-treated rats than sham rats, and significantly lower in cocktail-treated rats versus vehicle-treated rats (FIG. 9A). Similarly, the average number of TUNEL-positive cells was significantly higher in both regions of the hippocampus of vehicle-treated rats versus sham rats and was significantly lower in cocktail-treated rats versus vehicle-treated rats (FIG. 9B). These data support that the cocktail significantly mitigated brain morphological changes 72 h after a severe CA injury in rats.

Figure 10A:
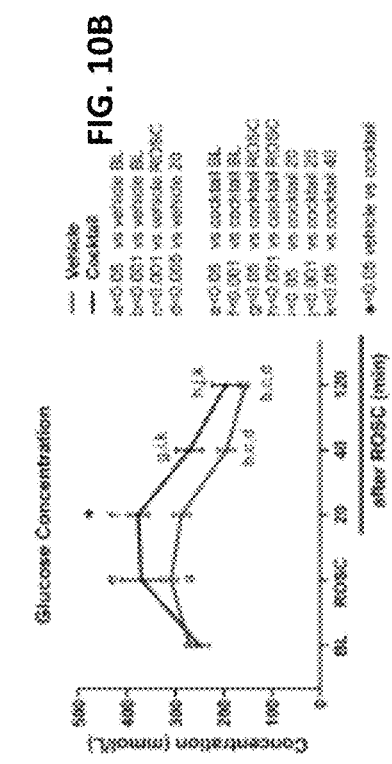
FIG. 10A-10D. Cocktail improves lactate, glucose, and hemodynamics after asphyxial cardiac arrest and resuscitation.
Figure 10B:
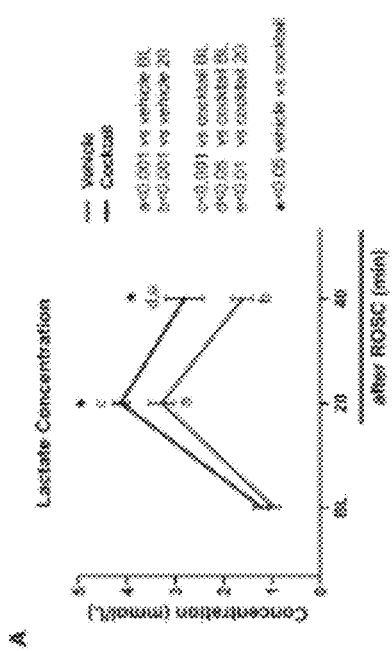

Cocktail Enhances Physiological Characteristics, Hemodynamics, and Arterial Blood Chemistry after Asphyxial Cardiac Arrest We assessed the general physiological characteristics of vehicle-treated and cocktail-treated rats (Tables 7-8). The baseline characteristics, time to achieve CA, or time to achieve ROSC did not significantly differ between vehicle-treated and cocktail-treated rats (Table 7). Arterial blood chemistry analysis showed minimal differences between vehicle-treated and cocktail-treated rats. The partial pressure of oxygen (pO2) was significantly lower in cocktail-treated (227.93±30.22 mmHg) versus vehicle-treated (384.08±35.93 mmHg) rats at 20 min post-ROSC (P<0.005). Oxygen saturation (SaO2) was significantly lower in cocktail-treated (94.86±1.27%) versus vehicle-treated (98.50±0.36%) rats at 40 minutes post-ROSC (P<0.05) (Table 8). Lactate levels were significantly higher in cocktail-treated (4.13±0.15 mmol/l) versus vehicle-treated (3.28±0.25 mmol/1) rats at 20 min post-ROSC, which was maintained at 40 min post-ROSC (cocktail-treated, 2.87±0.40 mmol/1; vehicle-treated, 1.61±0.21 mmol/1; P<0.05) (FIG. 10A). Blood glucose levels were greater in cocktail-treated (377.50±21.37 mg/dL) versus vehicle-treated (287.77±18.29 mg/dL) rats at 20 min post-ROSC (P<0.05), and the levels continued to decline until 120 min post-ROSC in both groups (FIG. 10B). Although lactate and glucose levels initially increased post-ROSC, there was a time-dependent, decreasing trend toward baseline in both groups.

TABLE 7

Baseline Arterial Blood Chemistry of Vehicle- and Cocktail-Treated Rats after Asphyxial Cardiac Arrest†

|  | Vehicle (n = 14) | Cocktail (n = 14) | P value |
| --- | --- | --- | --- |
| Baseline characteristics |  |  |  |
| Body weight, g | 450.6 ± 6.9 | 458.1 ± 7.2 | 0.46 |
| Mean arterial pressure, mmHg | 88.1 ± 4.0 | 89.1 ± 3.6 | 0.86 |
| Heart rate, bpm | 313.8 ± 13.5 | 295.9 ± 12.1 | 0.33 |
| Esophageal temperature, ° C. | 36.8 ± 0.1 | 36.9 ± 0.1 | 0.59 |
| Cardiac arrest characteristics |  |  |  |
| Time to cardiac arrest, sec | 184.0 ± 6.6 | 193.4 ± 6.6 | 0.27 |
| CPR time to ROSC, sec | 57.4 ± 2.2 | 57.9 ± 2.6 | 0.93 |

Abbreviations: CPR indicates cardiopulmonary resuscitation; HCO3— indicates bicarbonate; pCO2 indicates partial pressure of carbon dioxide; pO2 indicates partial pressure of oxygen; ROSC indicates return of spontaneous circulation; SaO2 indicates oxygen saturation.
*P < 0.05 and **P < 0.005 vs vehicle.
†Data expressed as mean ± SEM.

TABLE 8

Arterial Blood Chemistry of Vehicle- and Cocktail-Treated Rats after Asphyxial Cardiac Arrest† at Baseline, 20 min after ROSC and 40 min after ROSC

|  | | Time after ROSC | |
| --- | --- | --- | --- |
|  | Baseline | 20 min post-ROSC | 40 min post-ROSC |
| PH | | | |
| Vehicle | 7.42 ± 0.01 | 7.23 ± 0.01 | 7.34 ± 0.01 |
| Cocktail | 7.40 ± 0.01 | 7.18 ± 0.02 | 7.31 ± 0.02 |
| pCO2, mmHg | | | |
| Vehicle | 39.91 ± 1.60 | 52.23 ± 2.59 | 41.25 ± 1.64 |
| Cocktail | 43.36 ± 1.16 | 54.84 ± 3.28 | 41.80 ± 2.01 |
| pO2, mmHg | | | |
| Vehicle | 113.42 ± 7.97 | 384.08 ± 35.93 | 128.08 ± 9.33 |
| Cocktail | 109.71 ± 6.79 | 227.93 ± 30.22** | 106.29 ± 17.44 |
| HCO3—, mEq/L | | | |
| Vehicle | 25.86 ± 0.85 | 21.99 ± 0.56 | 22.13 ± 0.43 |
| Cocktail | 27.21 ± 0.53 | 20.62 ± 0.63 | 21.20 ± 0.47 |
| SaO2, % | | | |
| Vehicle | 98.08 ± 0.42 | 99.33 ± 0.67 | 98.50 ± 0.36 |
| Cocktail | 98.00 ± 0.38 | 97.36 ± 1.42 | 94.86 ± 1.27* |

Abbreviations: CPR indicates cardiopulmonary resuscitation; HCO3— indicates bicarbonate; pCO2 indicates partial pressure of carbon dioxide; pO2 indicates partial pressure of oxygen; ROSC indicates return of spontaneous circulation; SaO2 indicates oxygen saturation.
*P < 0.05 and **P < 0.005 vs vehicle.
†Data expressed as mean ± SEM.

Figure 10C:
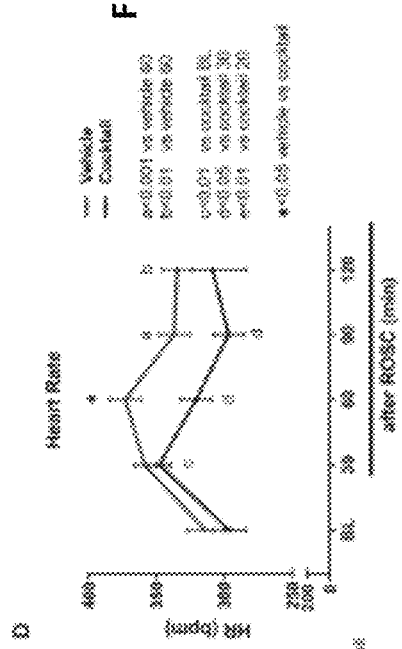
Figure 10D:
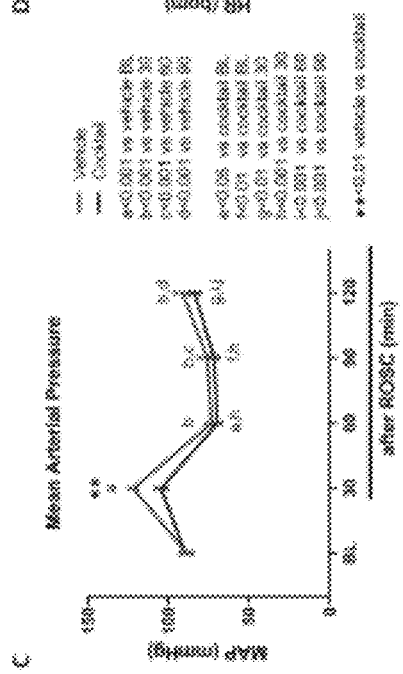

Compared to baseline, mean arterial pressure (MAP) increased in both groups at 30 min post-ROSC (vehicle-treated, 88.41±3.94 mmHg at baseline vs 121.64±2.94 mmHg at 30 min, P<0.0001; cocktail-treated: 89.07±3.63 mmHg at baseline vs 104.38±3.76 mmHg at 30 min P<0.05) (FIG. 10C). At 30 min post-ROSC, MAP was markedly lower in cocktail-treated (104.38±3.76 mmHg) versus vehicle-treated rats (121.64±2.94 mmHg; P<0.05) rats. In both groups, MAP returned to baseline values by 120 min post-ROSC. Compared with baseline values, heart rate (FIR) was higher in both groups at 120 min post-ROSC (vehicle-treated, 313.79±13.47 bpm at baseline vs 358.54±8.15 bpm at 120 min; P<0.05; cocktail-treated, 295.94±12.08 bpm at baseline vs 347.74±8.05 bpm at 120 min; P<0.005) (FIG. 10D). The HR was significantly different between the 2 groups only at 60 min post-ROSC (P<0.01). In vehicle-treated rats, the HR was highest at 60 min post-ROSC and then returned to baseline, whereas in cocktail-treated rats, the HR remained close to baseline values during the entire time course (FIG. 10D).

Discussion

In this study, we developed a novel cocktail therapy for treating CA. In a blinded, randomized, control study, we tested the efficacy of our newly formulated cocktail therapy in a severe-injury model of asphyxia-CA. Our results showed that our cocktail substantially improved 72 h survival as well as neurological function and brain morphology in these rats, supporting that our cocktail intervention improves neurologically intact survival after CA. Using a 12 min CA model aids in (1) inducing a severe injury that is expected to have a high mortality rate with a majority of surviving rats demonstrating severe neurofunctional deficits, and (2) is able to be resuscitated using conventional CPR; these two factors support the use of this model to validate the effectiveness of our cocktail therapy. The implementation of this severe CA model with the cocktail intervention supports shifting the paradigm of treating CA with one therapy that targets one change to using a cocktail therapy that targets multiple changes simultaneously.

To develop our multidrug cocktail, we formulated different drugs that have been individually shown to provide modest neuroprotection against ischemia-reperfusion injury.[12, 21-24] The task of formulating multiple drugs into one cocktail is intricate because of the balance between maximizing therapeutic efficacy with minimizing potential adverse effects. This was observed in our many trials to test the candidate formulations.

For the final formulation, we used MS to confirm the preservation of drugs in the formulation. Our MS analysis confirmed the presence of metformin, edavarone, zoniporide, cyclosporine A, N-acetyl cysteine, and vitamin C in the cocktail.

Furthermore, MS analysis did not detect any new peaks, except for traces of the formulation solvent PEG.[25] This finding suggests that no detectable drug-drug interactions exist in the system. Along with survival outcomes, we monitored changes in hemodynamics and blood chemistry after administering the cocktail. During development, some formulations showed a variety of therapeutic and adverse effects that resulted in poor outcomes. After various trials, we developed a formulation that maintained hemodynamics, such as MAP and HR, and blood chemistry parameters, such as pH, $pCO_2$, and $pO_2$, close to baseline levels. This is important because CA produces extremely abnormal physiology, and survival predicates on minimizing this severity. Our data show that although the cocktail can accomplish this goal, there was some alterations in lactate levels, suggesting that there is still room for further improvement.

Combination drug therapy is being discussed for a broad spectrum of conditions, including infectious diseases, diabetes, cancer, lipid disorders, rheumatologic conditions with the concept that targeting multiple components can produce a more robust outcome response.[26, 27] Despite advances in mechanical, technological, and pharmaceutical interventions for CA, the survival rate remains poor.[28] This low survival may be attributed to a lack of neurological protection, as the brain is severely impacted by factors such as mitochondrial dysfunction[3,8] increased generation of reactive oxygen species[3], metabolic disruptioe[9], and increased neuroinflammation[29]. Some studies have evaluated neuroprotection post-CA of either a single pharmaceutical agent therapy, such as SS-31, salubrinal, or cyclosporine A, or some combination of a few agents, such as ATP-magnesium chloride, ethanol-epinephrine-vasopressin (HBN-1), or argon-xenon.[30, 31] Although the polytherapy approach seems produce some positive survival and neurological outcomes post-CA, many of these therapies have not been able to overcome the complexity of mitigating global injury and have provided only minimal therapeutic benefit and thus have not been translated to human patients. One study in a model of swine ventricular fibrillation CA suggested that rapid administration of a "cocktail" containing epinephrine, vasopressin, amiodarone, sodium bicarbonate, and metoprolol seemed to produce more adverse effects and worse short-term outcomes than serial administration of epinephrine, vasopressin, amiodarone, and sodium bicarbonate.[32] Although this was an early study with an increased number of drugs, their cocktail design was not a combination in a single therapy; they used rapid administration of the drugs post-CA.

With an average of 12 years' time and significant amount of resources needed for drug discovery,[33] we believe that repurposing well-studied agents into one cocktail formulation is and attractive and feasible approach. Our study builds on these prior attempts at post-CA neuroprotection by showing the potential of a multidrug cocktail as a single therapy to improve outcomes after CA. Despite our positive survival and neuroprotective results, our study should be interpreted in the context of several limitations. First, we compared favorable post-CA outcomes between cocktail and vehicle without comparing outcomes using the individual drugs. Since our goal was to target multiple pathways simultaneously and prior studies have already used all of the drugs in our cocktail in a single administration, we elected to forgo the individual drug study. Second, we need to further explore the proposed mechanisms of each constituent in the cocktail. Although the drugs perform the intended actions to confer therapeutic efficacy, they may have other mechanisms of action that are either unknown or newly established when given in this formulation. Third, our MS analysis did not detect sulbutiamine, SS-31, CoQ10, or poloxamer 188 because these drugs are structurally complex and highly heterogeneous. We are currently developing more rigorous methodology for the identification of these compounds within the cocktail.

Since survival post-CA depends on how well other organs, besides the brain, are protected, our future goal is to determine how our cocktail may protect against injury in other organs and evaluate the therapeutic efficacy of cocktail as compared with serial injection of the induvial drugs. With respect to some of our limitations, this is the first report of a novel, multidrug cocktail that combines 10 distinct pharmaceutical agents that are evidence-based for targeting various injury-mediated alterations after CA into a single therapy in order to substantially improve neurologically intact survival in a severe model of rodent CA.

CONCLUSIONS

Our study describes the development and formulation of a multidrug cocktail that combines 10 drugs proven to target various individual pathways implicated in ischemia-reperfusion injury after CA. This cocktail improved neurologically intact survival at 72 h in a highly lethal rodent model of cardiac arrest. Our results support changing our approach from our current single agent therapies to using a multidrug cocktail to simultaneously treat multiple pathways affected by CA to confer neuroprotection and improve survival.

Supplemental Methods

Chemicals and Reagents

Drugs: Metformin (Sigma-Aldrich, USA), ATP-magnesium chloride (Sigma-Aldrich, USA), N-acetyl cysteine (Sigma-Aldrich, USA), poloxamer 188 (Sigma-Aldrich, USA), CoQ10 (Cayman Chemical, USA), cyclosporine A (Cayman Chemical, USA), Edaravone (Sigma-Aldrich, USA), SS-31 (Genemed Synthesis, USA), sulbutiamine (Toronto Research Chemical, Canada), vitamin C (Cayman Chemical, USA), and zoniporide (Toronto Research Chemical, Canada).

Detailed Animal Experimental Procedure for 12 Minutes of Asphyxial CA

Adult male Sprague-Dawley rats (400-500 g) were obtained from the Charles River Laboratory (Wilmington, MA, USA) and housed in the animal center of the Feinstein Institutes for Medical Research on a 12-hour light/dark cycle with free access to water and food. Rats were anesthetized with 4% isoflurane (Isothesia, Butler-Schein AHS), intubated with a 14-gauge plastic catheter (Surflo, Terumo Medical Corporation, NJ, USA), and placed on mechanical ventilation under 2% isoflurane. The left femoral artery and vein were cannulated with polyethylene catheters (PE50, BD Intramedic, USA) to monitor mean arterial pressure and aid in drug infusion. After surgical preparation and injecting heparin (300 IU), baseline physiologic parameters, such as MAP, HR, and end-tidal $CO_2$ ($ETCO_2$) were recorded using PowerLab and LabChart (ADInstruments, USA). The procedure for CA began with slowly injecting vecuronium bromide (2 mg/kg body weight; Hospira, USA) through the venous catheter over 4 min. Asphyxial-CA was induced by switching off the ventilator and then discontinuing isoflurane. After 12 min of asphyxial-CA, resuscitation was started, mechanical ventilation was resumed at 100% oxygen, and chest compressions were initiated. At the start of CPR, a bolus of epinephrine (20 µg/kg; International Medication System, Limited, USA) was injected through the venous catheter. CPR was continued until animals achieved ROSC, which was defined as MAP greater than 60 mmHg. If ROSC did not occur within 5 min after starting CPR, rats were excluded from the study. Hemodynamic recordings were continued until 2 h post-ROSC.

Blood samples were obtained from femoral artery at baseline, ROSC, and 20, 40, and 120 min post-ROSC. To analyze arterial blood gas, we measured pH, $pCO_2$, $pO_2$, bicarbonate, lactate, and SaO2 saturation at baseline, and 20 and 40 min post-ROSC. Blood glucose was measured at baseline, ROSC, and 20, 40, and 120 min post-ROSC. Then, 120 min post-ROSC, animals were extubated, decannulated, sutured, and provided postoperative care, which included subcutaneous saline and Buprenex (buprenorphine; 0.03 mg/kg body weight; Par Pharmaceutical, USA). Animals were returned to the animal housing facility and provided daily care according to the approved protocol. Animals were monitored for 72 h survival, and neurological function was evaluated at 24, 48, and 72 h post-ROSC by a blinded researcher using 2 scoring scales. Then rats were euthanized, and whole brain was harvested for histological analysis of neuronal degeneration.

Data Supplement

TABLE 9

Cocktail Development and Trials to Assess Survival Benefit

| Drug formulation number | Drugs included | Cocktail formulation | Study details | 72 h survival |
|---|---|---|---|---|
| NWH-1 | ATP-MgCl2, N-acetyl cysteine, sulbutiamine, zoniporide, cyclosporine A, CoQ10, vitamin C, and edaravone | CoQ10, cyclosporine A, and sulbutiamine were insoluble in water | Measured effects of each drug on hemodynamics and survival without inducing CA | Yes |

TABLE 9-continued

Cocktail Development and Trials to Assess Survival Benefit

| Drug formulation number | Drugs included | Cocktail formulation | Study details | 72 h survival |
|---|---|---|---|---|
| NWH-2 | ATP-MgCl2, N-acetyl cysteine, sulbutiamine, zoniporide, cyclosporine A, CoQ10, vitamin C, and edaravone | Formulation developed, but pH was not adjusted | Monitored hemodynamics and survival | Yes |
| NWH-3 | ATP-MgCl2, N-acetyl cysteine, poloxamer 188, SS-31, sulbutiamine, zoniporide, cyclosporine A, CoQ10, vitamin C, and edaravone | Drugs solubilized in 1X PBS, and pH was adjusted with sodium bicarbonate. | Monitored hemodynamics and survival after 12 min CA | Non-CA rats survived; CA rats died |
| NWH-4 | ATP-MgCl2, N-acetyl cysteine, poloxamer 188, SS-31, sulbutiamine, zoniporide, cyclosporine A, CoQ10, vitamin C, and edaravone | Cyclosporine A dissolved in 1X PBS, and pH adjusted with sodium bicarbonate. | Monitored survival after 12 min CA | No |
| NWH-5 | ATP-MgCl2, N-acetyl cysteine, poloxamer 188, SS-31, sulbutiamine, zoniporide, cyclosporine A, CoQ10, vitamin C, and edaravone | ATP-MgCl2 and zoniporide separately injected. Drugs solubilized in 1X PBS, and pH adjusted with sodium bicarbonate. | Monitored survival after 12 min CA | 1 CA rat survived; 3 CA rats died |
| NWH-6 | Metformin, ATP-MgCl2, N-acetyl cysteine, poloxamer 188, SS-31, sulbutiamine, zoniporide, cyclosporine A, CoQ10, vitamin C, and edaravone | ATP-MgCl2 separately injected. Drugs solubilized in 1X PBS, and pH adjusted with sodium bicarbonate. Metformin replaced sodium amobarbital. | Monitored survival after 12 min CA | No |
| NWH-7 | Metformin, ATP-MgCl2, N-acetyl cysteine, poloxamer 188, SS-31, sulbutiamine, zoniporide, cyclosporine A, CoQ10, vitamin C, edaravone, and hydrogen gas | ATP-MgCl2 separately injected. Drugs solubilized in 1X PBS, and pH adjusted with sodium bicarbonate. Hydrogen gas added. | Monitored survival after 10 min and 12 min | 110 min CA rat survived; CA 12 min CA rats died |
| NWH-8 | Metformin, ATP-MgCl2, N-acetyl cysteine, poloxamer 188, SS-31, sulbutiamine, zoniporide, cyclosporine A, CoQ10, vitamin C, edaravone, and hydrogen gas | ATP-MgCl2 removed. Drugs solubilized in 1X PBS, and pH adjusted with sodium bicarbonate. Hydrogen gas added. | Monitored survival after 10 min CA | 1 CA rat survived; 7 CA rats died |
| NWH-9 | Metformin, ATP-MgCl2, N-acetyl cysteine, poloxamer 188, SS-31, sulbutiamine, zoniporide, cyclosporine A, CoQ10, vitamin C, and edaravone | ATP-MgCl2 and hydrogen gas removed, Drugs solubilized in 1X PBS, and pH adjusted with sodium bicarbonate. | Monitored survival after 10 min and 12 min CA | All 3 10 min CA rats survived; all 5 12 min CA rats survived after cocktail treatment; all 5 12 min CA rats died after Vehicle treatment |

Abbreviations: ATP-MgCl2 indicates adenosine triphosphate-magnesium chloride; PBS indicates phosphate buffered saline.

TABLE 10

Scale 1-Modified Neurological Deficit Score for Rats*

| Parameter Characteristic Score | | | |
|---|---|---|---|
| General: 200 points | | | |
| Consciousness | Unresponsive = 0 | Depressed = 50 | Normal = 100 |
| Respiration, breaths per min | (<60, >120) = 100 | (<121, >140) = 50 | (>141) = 0 |
| Cranial nerves: 100 points | | | |
| Olfactory orient to smell | No = 0 | Yes = 20 | |
| Startle response to visual stimulus | No = 0 | Yes = 20 | |
| Corneal reflex blink response to corneal stimulus | No = 0 | Yes = 20 | |
| Whisker movement, spontaneous | No = 0 | Yes = 20 | |
| Hearing-startle response to loud noise | No = 0 | Yes = 20 | |
| Motor: 50 points | | | |
| Left forepaw-spontaneous or withdraw from pain | No = 0 | Yes = 1 0 | |
| Right forepaw-spontaneous or withdraw from pain | No = 0 | Yes = 1 0 | |
| Left hind paw-spontaneous or withdraw from pain | No = 0 | Yes = 1 0 | |
| Right hind paw-spontaneous or withdraw from pain | No = 0 | Yes = 1 0 | |
| Tail-spontaneous or withdraw from pain | No = 0 | Yes = 10 | |
| Sensory: 50 points | | | |
| Left forepaw-react to pain | No = 0 | Yes = 10 | |
| Right forepaw-react to pain | No = 0 | Yes = 10 | |
| Left hind paw-react to pain | No = 0 | Yes = 10 | |
| Right hind paw-react to pain | No = 0 | Yes = 10 | |
| Tail-react to pain | No = 0 | Yes = 10 | |
| Coordination: 100 points | | | |
| Ledge traverse | No = 0 | Yes = 25 | |
| Righting reflex | No = 0 | Yes = 25 | |
| Placing test | No = 0 | Yes = 25 | |
| Stop at table edge | No = 0 | Yes = 25 | |
| Total score | | | |

*Adapted from Neumar et al., 1995.

TABLE 11

Scale 2-Neurological Deficit Score*

| | |
|---|---|
| General behavioral deficit | Total score: 19 |
| Consciousness | Normal = 10 Stuporous = 5 Comatose or unresponsive = 0 |
| Arousal | Eyes open spontaneously = 3 Eyes open to pain = 1 No eye-opening = 0 |
| Respiration | Normal = 6 Abnormal (hypoventilation or hyperventilation) = 3 Absent = 0 |
| Brain stem function | Total score: 21 |
| Olfaction-response to smell of food | Present = 3 Absent = 0 |
| Vision-head movement to light | Present = 3 Absent = 0 |
| Pupillary reflex-pupillary light reflex | Present = 3 Absent = 0 |
| Corneal reflex | Present = 3 Absent = 0 |
| Startle reflex | Present = 3 Absent = 0 |
| Whisker stimulation | Present = 3 Absent = 0 |
| Swallowing, liquids or solids | Present = 3 Absent = 0 |
| Motor assessment-strength (test left and right separately) | Total score: 6 |
| | Normal = 3 Stiff or weak = 1 No movement or paralyzed = 0 |
| Sensory assessment-pain (test left and right separately) | Total score: 6 |
| | Brisk withdrawal with pain = 3 Weak or abnormal response (extension or flexion posture) = 1 No withdrawal = 0 |
| Motor behavior | Total score: 6 |
| Gait coordination | Normal = 3 Abnormal = 1 Absent = 0 |
| Balance beam walking | Normal = 3 Abnormal = 1 Absent = 0 |
| Behavior | Total score: 12 |
| Righting reflex | Normal = 3 Abnormal = 1 Absent = 0 |
| Negative geotaxis | Normal = 3 Abnormal = 1 Absent = 0 |
| Visual placing | Normal = 3 Abnormal = 1 Absent = 0 |
| Turning alley | Normal = 3 Abnormal = 1 Absent = 0 |
| Seizures | Total score: 10 |
| Convulsive or non-convulsive | No seizure = 10 Focal seizure = 5 General seizure = 0 |

*Described in Jia et al. 2008.

REFERENCES

1. Benjamin E J, et al. *Neurol Clin.* 2006; 24:73-87, vi.
2. Han F, et al. *Crit Care Med.* 2008; 36:S447-53.
3. Nakka V P, et al. *Neurotox Res.* 2010; 17:189-202.
4. Jiang J, et al. *Biomed Res Int.* 2014; 2014:192769.
5. Vereczki V, et al. *J Cereb Blood Flow Metab.* 2006; 26:821-35.
6. Xiang Y, et al. *Biomed Rep.* 2016; 5:11-17.
7. Choi J, et al. *J Am Heart Assoc.* 2019; 8:e012809.
8. Shoaib M, et al. *Sci Rep.* 2020; 10:19707.
9. Lundin A, et al. *Eur Heart J Cardiovasc Pharmacother.* 2016; 2:54-75.
10. Katz L M, et al. *Resuscitation.* 2015; 92:26-31.
11. Liu J, et al. *Am J Emerg Med.* 2016; 34:1080-5.
12. Li L, et al. *Mot Neurobiol.* 2018; 55:2042-2055.
13. Arts E J and Hazuda D J. *Cold Spring Harb Perspect Med.* 2012; 2:a007161.
14. Preissner S, et al *PLoS One.* 2012; 7:e51020.
15. Weinreich D M, et al. *N Engl J Med.* 2020.
16. Ferslew K. Specimen Preparation/Extraction. In: B. S. Levine, Kerrigan, Sarah, ed. Principles of Forensic Toxicology. Fifth ed.: Springer *Nature* 2020: 109-125.
17. Han F, et al. *Resuscitation.* 2010; 81:93-9.
18. Neumar R W B N, et al. *Resuscitation.* 1995; 29:249-63.
19. Jia X, et al. *Resuscitation.* 2008; 76:431-42.
20. Zhu J, et al. *J Am Heart Assoc.* 2018; 7.
21. Knapp J, et al. *Shock.* 2015; 43:576-81.
22. Zhang W, et al. *Heart Lung Circ.* 2019; 28:505-508.
23. Ikeda K, et al. *Resuscitation.* 2016; 105:138-44.
24. Marcos M A, et al. *Nanomaterials (Basel).* 2017; 8.
25. Ascierto P A and Marincola F M. *J Transl Med.* 2011; 9:115.
26. Rationalizing Combination Therapies. *Nat Med.* 2017; 23:1113.
27. Shoaib M and Becker L B. A Walk Through the Progression of Resuscitation Medicine. Ann NY *Acad Sci.* 2020.
28. Xu M, et al. *Inflammation.* 2016; 39:1594-602.
29. Choudhary R C, et al. *Frontiers in Medicine.* 2021; 8.
30. Hayashida K, et al. *Front Med (Lausanne).* 2020; 7:586229.
31. Mader T J, et al. *Prehosp Emerg Care.* 2016; 20:390-8.
32. Kraljevic S, et al. *EMBO Rep.* 2004; 5:837-42.
33. Choi Y H, et al. *J Pharm Sci.* 2006; 95:2543-52.
34. He F, et al. *J Inflamm (Lond).* 2020; 17:25.
35. Walters T J, et al. *J Trauma.* 2011; 70:1192-7.
36. Belousova M, et al. *J Cardiovasc Pharmacol.* 2016; 67:103-9.
37. Qin T, et al. *Am J Emerg Med.* 2016; 34:1944-1949.
38. Sabbah H N, et al. *Circ Heart Fail.* 2016; 9:e002206.
39. Trovero F, et al. *Neurosci Lett.* 2000; 292:49-53.
40. Tsai M S, et al. *Acad Emerg Med.* 2014; 21:257-65.
41. Lamoureux L, et al. *Circulation.* 2014; 130:A148-A148.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety. Further embodiments are set forth in the following claims.

What is claimed is:

1. A method of providing neuroprotection to a brain of a subject suffering from, having suffered from, or at risk of suffering from, cerebral ischemia, wherein an effective amount of each of the following therapeutic agents: metformin, N-acetyl cysteine, vitamin C, edaravone, polaxamer 188, SS-31, CoQ10, cyclosporin A, sulbutiamine, and zoniporide, or pharmaceutically acceptable salts of any thereof, is administered to the subject concurrently as more than one composition.

2. A method of providing neuroprotection to a brain of a subject suffering from, having suffered from, or at risk of suffering from, cerebral ischemia, comprising administering to the subject a formulation prepared by mixing together in one composition an effective amount of each of the following therapeutic agents: metformin, N-acetyl cysteine, vitamin C, edaravone, polaxamer 188, SS-31, CoQIO, cyclosporin A, sulbutiamine, and zoniporide, or pharmaceutically acceptable salts of any thereof.

3. The method of claim 2, wherein the therapeutic agents are in the formulation in a mass ratio of:
metformin: N-acetyl cysteine: poloxamer 188: coenzymeQ10 (CoQ10):
cyclosporin A: edaravone: elamipretide (SS-31): sulbutiamine: vitamin C:
zoniporide
of
about 80 to about 120: about 120 to about 180: about 120 to about 180: about 24 to about 36: about 8 to about 12: about 2.4 to about 3.6: about 0.4 to about 0.6: about 10 to about 15: about 80 to about 120: about 2.4 to about 3.6.

4. The method of claim 2, wherein the therapeutic agents are in the formulation in a mass ratio of:
metformin: N-acetyl cysteine: poloxamer 188: coenzymeQ10 (CoQ10):
cyclosporin A: edaravone: elamipretide (SS-31): sulbutiamine: vitamin C:
zoniporide
of
about 100: about 150: about 150: about 30: about 10: about 3: about 0.5: about 12.5: about 100: about 3.

5. The method of claim 1, wherein the effective amount of each therapeutic agent is, in milligrams per kg of subject mass:
metformin: about 80 mg/kg to about 120 mg/kg;
N-acetyl cysteine: about 120 mg/kg to about 180 mg/kg;
poloxamer 188: about 120 mg/kg to about 180 mg/kg;
CoQ10: about 24 mg/kg to about 36 mg/kg;
cyclosporine A: about 8 mg/kg to about 12 mg/kg;
edaravone: about 2.4 mg/kg to about 3.6 mg/kg;
SS-31: about 0.4 mg/kg to about 0.6 mg/kg;
sulbutiamine: about 10 mg/kg to about 15 mg/kg;
vitamin C: about 80 mg/kg to about 120 mg/kg; and
zoniporide: about 2.4 mg/kg to about 3.6 mg/kg.

6. The method of claim 1, wherein the effective amount of each therapeutic agent is, in milligrams per kg of subject mass
metformin: about 100 mg/kg;
N-acetyl cysteine: about 150 mg/kg;
poloxamer 188: about 150 mg/kg;
CoQ10: about 30 mg/kg;
cyclosporin A: about 10 mg/kg;
edaravone: about 3 mg/kg;
SS-31: about 0.5 mg/kg;
sulbutiamine: about 12.5 mg/kg;
vitamin C: about 100 mg/kg; and
zoniporide: about 3 mg/kg.

7. The method of claim 2, wherein the effective amount of each therapeutic agent is, in milligrams per kg of subject mass:
metformin: about 80 mg/kg to about 120 mg/kg;
N-acetyl cysteine: about 120 mg/kg to about 180 mg/kg;
poloxamer 188: about 120 mg/kg to about 180 mg/kg;
CoQ10: about 24 mg/kg to about 36 mg/kg;
cyclosporine A: about 8 mg/kg to about 12 mg/kg;
edaravone: about 2.4 mg/kg to about 3.6 mg/kg;
SS-31: about 0.4 mg/kg to about 0.6 mg/kg;
sulbutiamine: about 10 mg/kg to about 15 mg/kg;
vitamin C: about 80 mg/kg to about 120 mg/kg; and
zoniporide: about 2.4 mg/kg to about 3.6 mg/kg.

8. The method of claim 2, wherein the effective amount of each therapeutic agent is, in milligrams per kg of subject mass
metformin: about 100 mg/kg;
N-acetyl cysteine: about 150 mg/kg;
poloxamer 188: about 150 mg/kg;
CoQ10: about 30 mg/kg;
cyclosporin A: about 10 mg/kg;
edaravone: about 3 mg/kg;
SS-31: about 0.5 mg/kg;
sulbutiamine: about 12.5 mg/kg;
vitamin C: about 100 mg/kg; and
zoniporide: about 3 mg/kg.

* * * * *